US010908341B2

(12) United States Patent
Rose et al.

(10) Patent No.: US 10,908,341 B2
(45) Date of Patent: *Feb. 2, 2021

(54) FRONTAL LIGHT DIFFUSING DEVICE FOR USE IN PHOTOIMMUNOTHERAPY

(71) Applicant: Rakuten Medical, Inc., San Diego, CA (US)

(72) Inventors: Andreas Rose, Herborn (DE); Kyle Johnston, Sammamish, WA (US); Merrill Biel, Mendota Heights, MN (US)

(73) Assignee: Aspyrian Therapeutics Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/701,394

(22) Filed: Dec. 3, 2019

(65) Prior Publication Data

US 2020/0166690 A1 May 28, 2020

Related U.S. Application Data

(63) Continuation of application No. 15/790,110, filed on Oct. 23, 2017, now Pat. No. 10,527,771.
(Continued)

(51) Int. Cl.
*F21V 8/00* (2006.01)
*G02B 6/02* (2006.01)
(Continued)

(52) U.S. Cl.
CPC .......... *G02B 6/0008* (2013.01); *A61N 5/062* (2013.01); *G02B 6/001* (2013.01); *G02B 6/02* (2013.01);
(Continued)

(58) Field of Classification Search
None
See application file for complete search history.

(56) References Cited

U.S. PATENT DOCUMENTS 5,751,869 A * 5/1998 Li ........................ A61B 90/35
385/33
5,978,541 A 11/1999 Doiron
(Continued)

FOREIGN PATENT DOCUMENTS

DE 197 39 456 A1 3/1999
DE 20 2015 009023 U1 7/2016
(Continued)

OTHER PUBLICATIONS

Bolesh J. Skutnik, Non-Circular Core, All Silica Fibers for Irradiation and Sensing Medical Applications, (2013).
(Continued)

*Primary Examiner* — Ashok Patel
(74) *Attorney, Agent, or Firm* — The Dobrusin Law Firm, PC

(57) ABSTRACT

The present invention provides a frontal light diffusing device comprising a non-circular core fiber section having a proximal end and a distal end, and a lens; wherein fiber core of the non-circular core section has a "top hat" core irradiance distribution and the frontal light diffusing device provides a "top hat" spatial irradiance distribution at a targeted location. The present invention further provides a frontal light diffusing device comprising an optical fiber and a collimation lens assembly wherein the collimation lens assembly includes a variable aperture that blocks portions of light outcoupled from the optical fiber thereby allowing only a central portion of the light to exit through the variable aperture resulting in a flat irradiance distribution.

27 Claims, 38 Drawing Sheets

Related U.S. Application Data

(60) Provisional application No. 62/529,507, filed on Jul. 7, 2017, provisional application No. 62/412,606, filed on Oct. 25, 2016.

(51) Int. Cl.
*G02B 6/036* (2006.01)
*G02B 6/26* (2006.01)
*G02B 6/24* (2006.01)
*A61N 5/06* (2006.01)
*A61N 5/067* (2006.01)

(52) U.S. Cl.
CPC ......... *G02B 6/02314* (2013.01); *G02B 6/036* (2013.01); *G02B 6/262* (2013.01); *A61N 2005/063* (2013.01); *A61N 2005/067* (2013.01); *G02B 6/241* (2013.01)

(56) References Cited

U.S. PATENT DOCUMENTS

| | | | |
|---|---|---|---|
| 6,270,492 B1 | 8/2001 | Sinofsky | |
| 7,167,630 B2 | 1/2007 | Eyal | |
| 8,831,396 B1 | 9/2014 | Price | |
| 10,527,771 B2 * | 1/2020 | Rose | G02B 27/0927 |
| 2004/0151008 A1 * | 8/2004 | Artsyukhovich | A61F 9/00823 362/572 |
| 2007/0147758 A1 | 6/2007 | Cummings | |
| 2008/0158905 A1 | 7/2008 | Chuang | |
| 2009/0210038 A1 | 8/2009 | Neuberger | |
| 2012/0330107 A1 | 12/2012 | Vayser | |
| 2013/0170806 A1 | 7/2013 | Denner | |
| 2013/0197473 A1 | 8/2013 | McMillan | |
| 2016/0106504 A1 | 4/2016 | Casalino | |
| 2018/0042459 A1 | 2/2018 | Loiselle | |

FOREIGN PATENT DOCUMENTS

| | | |
|---|---|---|
| JP | S59137069 A | 8/1984 |
| JP | 2005056608 A | 3/2005 |
| JP | 2006039043 A | 2/2006 |
| JP | 2007102058 A | 4/2007 |
| JP | 2009168914 A | 7/2009 |
| JP | 2015009031 A | 1/2015 |
| JP | 2015500571 A | 1/2015 |
| JP | 2016030009 A | 3/2016 |
| JP | 2016051059 A | 4/2016 |
| JP | 2016067492 A | 5/2016 |
| JP | 2016078043 A | 5/2016 |
| JP | 2020500575 A | 1/2020 |
| WO | 99/23041 A1 | 5/1999 |
| WO | 2010/019800 A1 | 2/2010 |

OTHER PUBLICATIONS

Extended Search Report dated May 12, 2020 (Application No. 19214413.7).
Spie Europe Ltd: "Non-Circular Core Silica Optical Fibers", Feb. 26, 2014, XP055437965, Retrieved from the Internet: URL:http://optics.org/products/P000020241 [retrieved on Jan. 3, 2018].
Bronislav Hracek et al: "New Ways to Generate Flat-Top Profiles", Optik & Photonik, Dec. 1, 2015, pp. 16-18, XP055437968, DOI: 10.1002/opph.201500037 Retrieved from the Internet: URL:http://onlinelibrary.wiley.com/store/10.1002/opph201500037/asset/16_ftp.pdf?.
Europe North Ceramoptec: "Optran NCC UV/WF", Mar. 25, 2011, XP055438077, Retrieved from the Internet: URL:http://vertassets.blob.core.windows.net/download/.
PCT Search Report & Written Opinion dated Mar. 12, 2018, Application No. PCT/US2017/057787.
PCT Sear Report Written Opinion dated Jul. 16, 2018, Application No. PCT/US2018/029054.

* cited by examiner

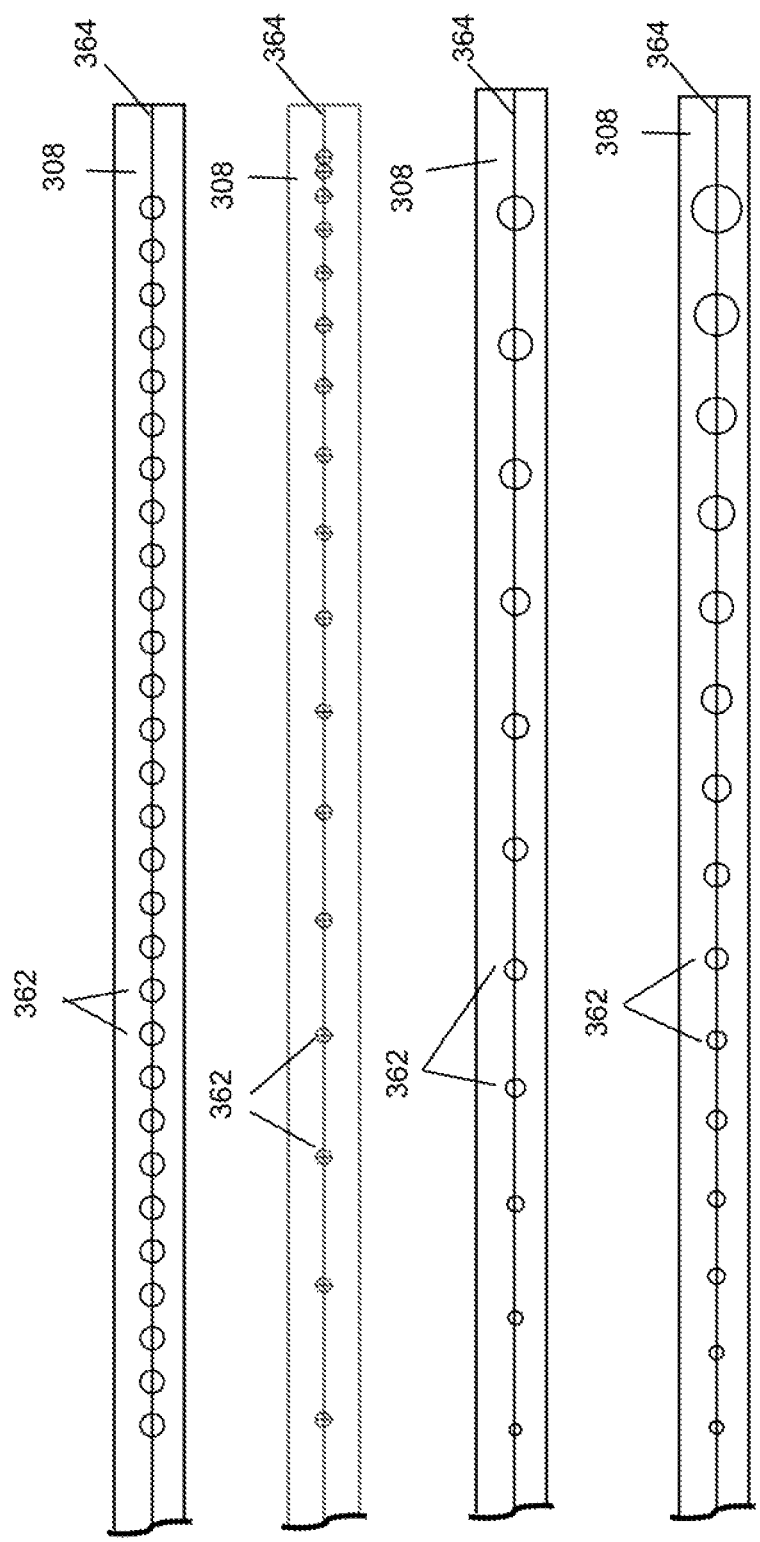

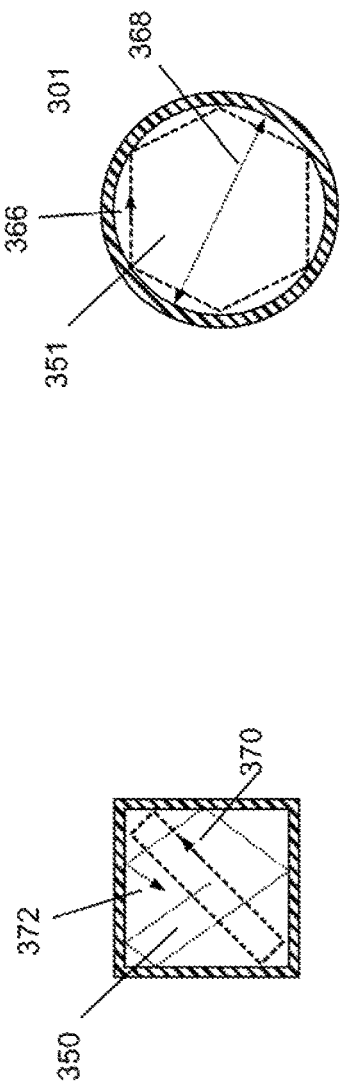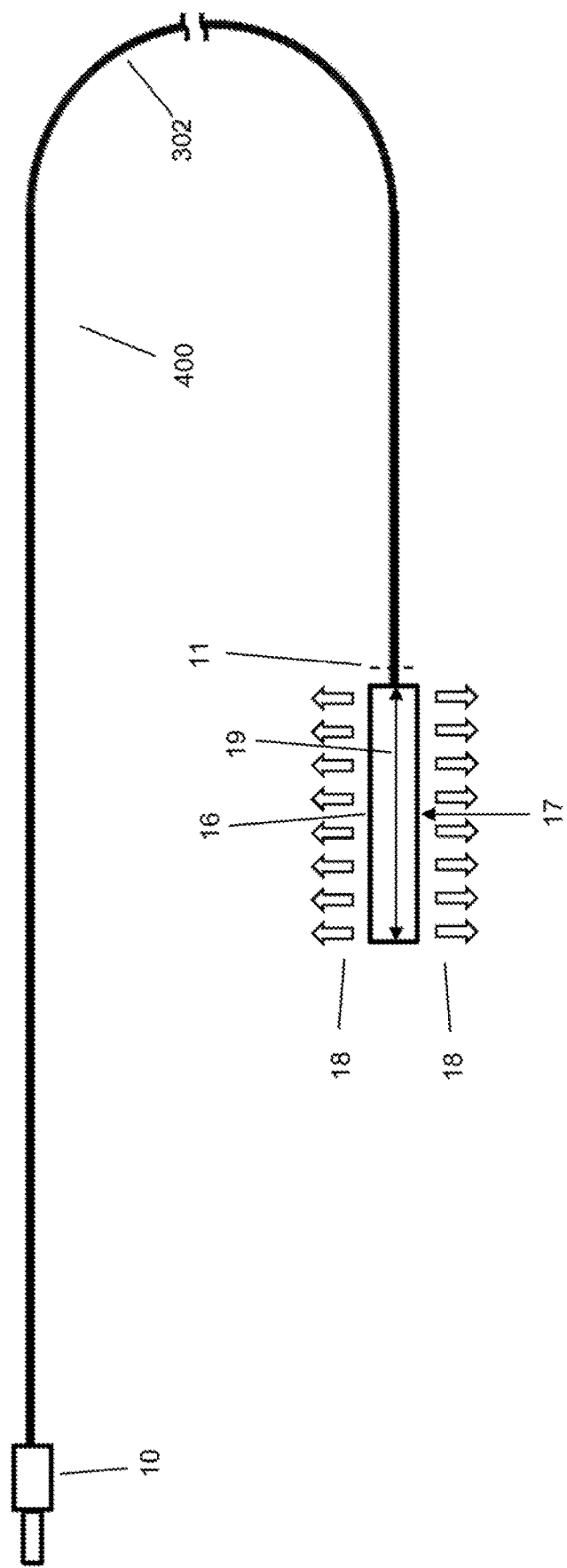

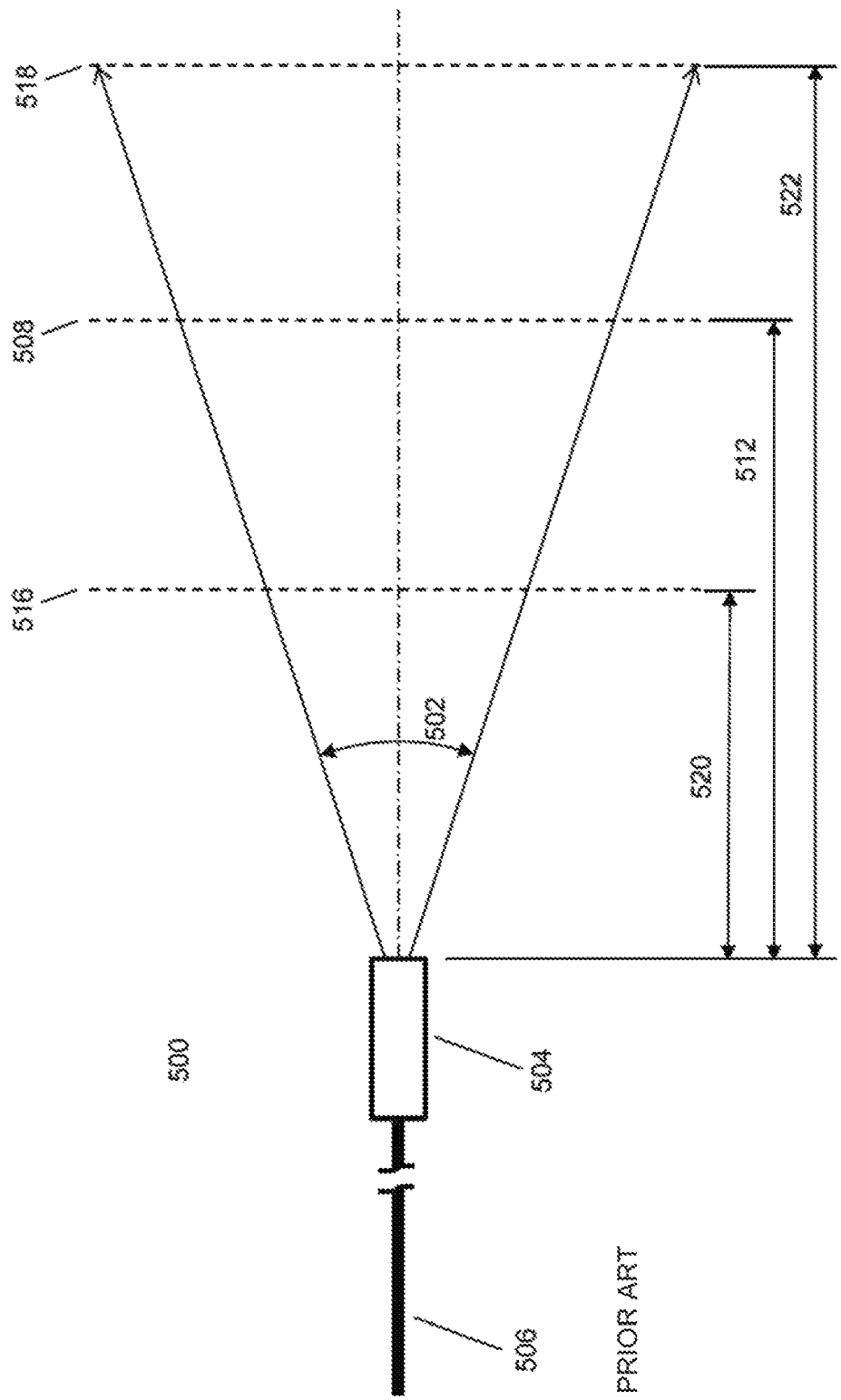

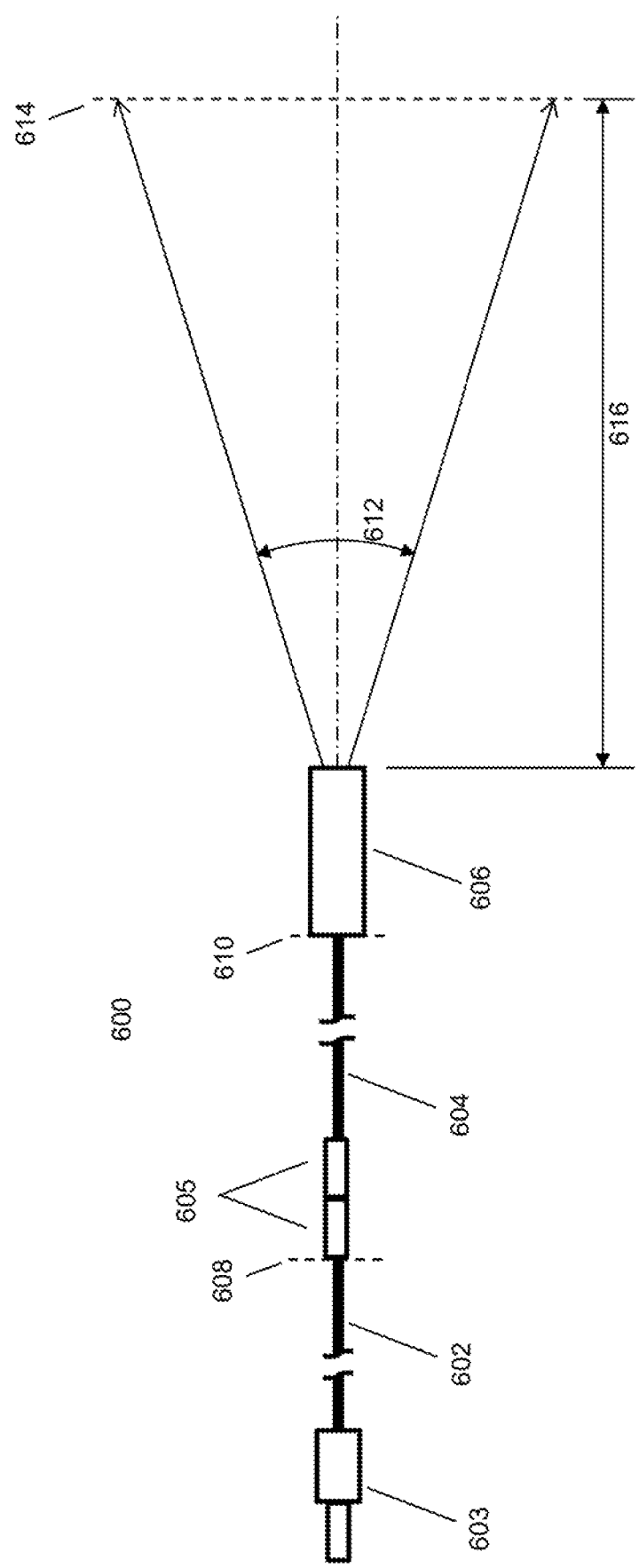

FRONTAL LIGHT DIFFUSING DEVICE FOR USE IN PHOTOIMMUNOTHERAPY

CLAIM OF BENEFIT OF FILING DATE

This application is a continuation U.S. patent application Ser. No. 15/790,110 filed on Oct. 23, 2017, which claims the benefit of the filing date of U.S. Provisional Application Ser. No. 62/412,606 titled: "Light Diffusing Device for Use in Photoimmunotherapy" filed on Oct. 25, 2016 and U.S. Provisional Application Ser. No. 62/529,507 titled: "Frontal Light Diffusing Device for Use in Photoimmunotherapy" filed on Jul. 7, 2017, which are incorporated herein by reference for all purposes.

FIELD OF INVENTION

The present invention relates to a medical device for performing photoimmunotherapy ("PIT"), photodynamic therapy ("PDT") or other light activated treatments upon tissue of an organism, cellular or acellular organisms and methods of using such medical device in PIT, PDT or other light activated therapies. More particularly, the invention is a fiber optic diffuser device to deliver light in a desired illumination pattern and wavelength for PIT, PDT or other light therapies to an area under treatment.

BACKGROUND OF THE INVENTION

PIT, PDT and other light activated therapies have been used to treat various maladies and diseases. PIT and PDT and other light activated therapies often involve the use of an exogenous or endogenous photosensitizing agent or substance that is activated by electromagnetic radiation (e.g., light such as laser light, LED light, etc.). PIT is based on a new drug system that consists of a cancer targeting monoclonal antibody conjugated to a photoactivatable molecule. The targeting agent can include other moieties such as ligands, viral capsid, peptides, liposomes, nanoparticles, etc. This drug conjugate is not pharmacologically active until the conjugate is bound to the cancer cells and gains anticancer activity upon light-mediated activation at the tumor site. Tumor targeting and context precision activation of the drug provides exquisite cancer specificity and permits rapid cancer cell killing without damage to the surrounding healthy tissues. Anticancer activity of PIT is highly effective and it works with multiple types of monoclonal antibodies and other targeting moieties, thus the platform enables the targeting of a broad range of cancer antigens and tumor types. It should be noted that the present invention is not limited to targeting tumor sites. Instead, the present invention can also be used to target other cellular and acellular organisms including bacteria, fungi, viruses, prions, etc. in order to treat or prevent disease(s).

The basic requirements for PIT and/or PDT light sources are to match the activation spectrum of the exogenous or endogenous photosensitizer (usually the wavelength of peak absorbance) and to generate adequate power at this wavelength, deliverable to the target tissue ergonomically and with high efficiency. Typically, 1-5 W of usable power are required in the 630-850 nm range at irradiances of up to several hundred mW cm$^{-2}$ in order to deliver treatments in tens of minutes. In addition, the sources must be reliable in the clinical environment and be cost-effective.

For illumination of the area to be treated ("treatment area"), usually cylindrical and frontal (superficial) diffusers, sometimes also called "micro lens diffusers", are generally used. The fiber optic cylindrical (side firing) and superficial (front firing) diffusers consist of multimode fiber assemblies with a round core/cladding structure from 50-1000 um core diameter with attached diffusing section that can be connected directly to a light source, for instance by means of an optical connector.

I. Conventional Cylindrical Light Diffusers

FIG. 1 shows an example of a typical commercially available cylindrical light diffusing device 100 comprising an optical connector 10 connecting to a light source (not shown) on one end, an optical fiber 12 and a cylindrical diffuser 16 on the other end. During operation, the optical fiber 12 is in light communication with the cylindrical diffuser 16 causing the cylindrical diffuser 16 to out-couple light in a longitudinally radial-symmetric irradiance distribution 18 across the longitudinal length 19 of the cylindrical diffuser 16.

A map of the irradiance at a vertical (i.e., latitudinal) cross-section (shown as "11" in FIG. 1) through the core of the optical fiber 12 taken just before the optical fiber 12 enters the cylindrical diffuser 16 is shown in FIG. 2. In this exemplary embodiment, the light source used is a 690 nm laser with 1 Watt launch power and this power was adjusted until the irradiance 18 measured at the center 17 of the longitudinal length of the diffuser 16 was 150 mW/cm$^2$. This measurement is taken 0.75 mm from the central axis of the stated location of the diffuser 16. The optical fiber 12 from the light source leading up to the cylindrical diffuser 16 ("lead fiber") is 2 meters long. The optical fiber 12 has a 700 µm outer diameter ("OD") glass core and a 740 µm OD cladding. During operation, the optical fiber 12 is filled with laser light having an angular distribution of a numerical aperture ("NA") of 0.22. The cross-section 11 was taken after 2 meter lead fiber (12). The associated irradiance distribution graphs of FIG. 2 taken from vertical and horizontal cross sections through the center of the map of the irradiance show that there is poor spatial uniformity of the irradiance distribution in the core of the optical fiber 12 ("core irradiance distribution"). The large values in the center of the graphs show that there is significantly higher irradiance in the center of the fiber core than near its edges. The graph on the top of FIG. 2 shows the irradiance distribution of the horizontal cross section while the graph on the right side of FIG. 2 shows the irradiance distribution of the vertical cross section. As shown in FIG. 2, both graphs have two axes: one axis shows width (e.g., diameter) in mm and the other axis shows irradiance in Watt/cm$^2$.

Not only does the core irradiance distribution of the optical fiber 12 have poor spatial uniformity, the out-coupled longitudinally radially-symmetric irradiance distribution along the outer surface of irradiance emitting section of the cylindrical diffuser 16 ("diffusing irradiance distribution") also demonstrates poor spatial uniformity leading to a non-ideal irradiance distribution as shown in FIG. 3. This uneven irradiance distribution is undesirable because the irradiance uniformity would not satisfy the needs of a proper "dosimetry", meaning the correct irradiance in light power/surface area for an optimal medical treatment efficacy. In FIG. 3, the horizontal axis shows the longitudinal length (in mm) used to measure the length 19 of the cylindrical diffuser 16 and the vertical axis shows the out-coupled irradiance at the surface of the cylindrical diffuser 16 measured in Watts/cm$^2$ at a distance 0.75 mm from the central axis.

FIG. 4 is an example for a typical commercially available cylindrical light diffusing device 200 comprising an optical connector 20 connecting to a light source (not shown) on one end, an optical fiber 22 and a cylindrical diffuser 26 on the other end. During operation, the optical fiber 22 is in light communication with a mode mixer 24 and the cylindrical diffuser 26 causing the cylindrical diffuser 26 to out-couple light in a longitudinally radial-symmetric irradiance distribution 28 across the longitudinal length 29 of the cylindrical diffuser 26.

FIG. 5 shows a map of the irradiance at a vertical cross-section (shown as "21" in FIG. 4) through the core of the optical fiber 22 taken just before the optical fiber 22 enters the cylindrical diffuser 26. In this exemplary embodiment, the light source used is a 690 nm laser with 1 Watt launch power and this power was adjusted until the irradiance 28 measured at the center 27 of the longitudinal length of the diffuser 26 was 150 mW/cm$^2$. This measurement is taken 0.75 mm from the central axis of the stated location of the diffuser 26. The optical fiber 22 from the light source leading up to the cylindrical diffuser 26 ("lead fiber") is 2 meters long. The optical fiber 22 has a 700 μm OD glass core and a 740 μm OD cladding. During operation, the optical fiber 22 is filled with laser light having an angular distribution of a numerical aperture ("NA") of 0.22. The cross-section 21 was taken after 2 meter lead fiber (22). Unlike FIG. 2, the associated irradiance distribution graphs shown in FIG. 5 taken from vertical and horizontal cross sections through the center of the map of the irradiance show that when a mode mixer (24) is used with the optical fiber 22, a "top hat" irradiance distribution profile is achieved (i.e., variation of the irradiance distribution of the entire cross-section is less than +/−20% of the average irradiance), indicating a high degree of uniformity of the irradiance distribution in the core of the fiber 22 (e.g. optimal core irradiance distribution). Similar to FIG. 2, the graph on the top of FIG. 5 shows the irradiance distribution of the horizontal cross section while the graph on the right side of FIG. 5 shows the irradiance distribution of the vertical cross section. As shown in FIG. 5, both graphs have two axes: one axis shows width (e.g., diameter) in mm and the other axis shows irradiance in Watt/cm$^2$.

In contrast to the graph shown in FIG. 3, the out-coupled longitudinally radially-symmetric irradiance distribution along the outer surface of irradiance emitting section of the cylindrical diffuser 26 (e.g., the diffusing irradiance distribution) shows spatial uniformity leading to an optimal "top hat" diffusing irradiance distribution as shown in FIG. 6. FIG. 6 shows that the variation of the out-coupled irradiance distribution should be a "top hat" with less than +/−20% of the average ("$I_0$") optical irradiance for a cylindrical diffuser in terms of the radially emitted irradiance distribution (e.g., optimal diffusing irradiance distribution). The horizontal axis of FIG. 6 shows longitudinal length in mm and the horizontal arrow indicates the length 29 of the cylindrical diffuser 26. The vertical axis of FIG. 6 shows the out-coupled irradiance at the surface of the cylindrical diffuser 26 measured in Watts/cm$^2$ at a distance 0.75 mm from the central axis.

As shown above, in order to achieve the "top hat" diffusing irradiance distribution for a conventional cylindrical diffuser, optimal mode mixing (e.g., with an effective mode mixer) in the optical fiber is required. The mode mixer 24 shown in FIG. 4 is created in the optical fiber 22 by a series of five consecutive alternating tight radius bends. Another conventional mode mixing method (not shown) is to wrap the optical fiber 22 tightly multiple times around an object (e.g. a mandrel). These popular forms of mode mixing create spatial uniformity at the expense of increased transmission losses, often resulting in the losses of 50% or more. Additionally, these techniques also create stress points within the optical fiber 22. Applying stress to an optical fiber is problematic because it can lead to irreversible damage to such optical fiber, as the micro-bending pushes the optical fiber bending force to the maximum fatigue limit of the glass fiber. Furthermore, these cylindrical diffuser fiber assemblies are sometimes used with optical power that can exceed 1 Watt, which lowers the maximum fatigue limits even more due to thermal heating from the light lost from the fiber core. This thermal heating issue can adversely impact both glass and polymer materials. Thermally destroyed mode mixers have occurred in practice, which represents one major driver to substitute these conventional mode mixers with an alternative according to the described invention.

Please note that an effective mode mixer by itself is insufficient to achieve the "top hat" diffusing irradiance distribution. An effective light diffuser or diffusing section is also required. For cylindrical diffusers, the diffuser section commonly uses additional elements and/or processing of the diffuser section in order to achieve the "top hat" diffusing irradiance distribution. As shown in FIG. 7, one conventional method is removing the cladding of the fiber tip 30 (the diffusing section) and etching the exposed fiber core with hydrofluoric acid or grinding it on a polishing apparatus. The resulting conical tip with its frosted appearance is then covered with a protective transparent envelope 32. Referring to FIG. 8, another conventional method is manufacturing a separate diffuser 34 containing scattering medium 36 that is composed of micron-sized titanium oxide ($TiO_2$) particles embedded in clear epoxy or silicone elastomer, which is encased in a protective Teflon sheath 38. A reflector 40 attached to a plastic plug 42 is then inserted into the open distal end of the sheath 38. The purpose of the coated plug 42 is to reflect any light that survives forward propagation back through the scattering medium 36 where it can be re-distributed, thus improving the uniformity of the emission profile. Yet another method of construction can be described as a hybrid of the two previous methods wherein the cladding of an optical fiber is removed mechanically leaving the surface of the core roughened. This surface is then coated with a silicone elastomer on to which a second layer of elastomer impregnated with titanium oxide particles is deposited. Finally, the entire diffusing tip is encased in an outer PTFE tube which in turn is terminated with a reflective end cap in a manner similar to the above-described method and shown in FIG. 8. These described techniques are costly, labor intensive and time consuming. Hence, these light diffusers are very expensive.

It should be noted there exist other conventional techniques to provide a light diffuser that can produce the "top hat" diffusing irradiance distribution such as having light scattering features on the outside of the optical fiber surface (e.g., divots, threads, notches, general roughening, or the like). These techniques are labor intensive and the resulting homogeneity of the light output pattern relies strongly on a constant fiber diameter, which can vary by up to +/−5%, making it cumbersome to achieve constant and repeatable results in the manufacturing process.

II. Conventional Frontal Light Diffusers

Referring to FIG. 37A, an exemplary embodiment of a typical frontal (superficial) diffuser 500 is provided with 690 nm light introduced onto an optical fiber 506 (e.g., a cylindrical optical fiber) with a 550 um diameter core via a fiber optic connector 503. A ¼ pitch, 1 mm diameter graded index ("GRIN") lens component 504 located at the distal end output face 510 of the optical fiber 506 generates the outcoupled light 502. Since the desired treatment area (i.e., target) 508 has a much larger diameter (e.g. 42 mm) than the diameter of the optical fiber 506 (e.g. 550 um), the effect of the lens component 504, to a first approximation, is to form an image of the output face 510 of the optical fiber 506 onto the target 508 where the target 508 is located at some standoff distance 512 (e.g., 64 mm) away from the lens component 504. In this fashion, the spatial irradiance distribution of a cross section along the target 508, as shown in FIG. 37C, is closely related to the spatial irradiance distribution along a cross section of 510, as shown in FIG. 37B. Note that this exemplary embodiment exhibits low loss (e.g., −0.25 dB), where 1.0 Watt input power is enough to generate the irradiance distribution in FIG. 37C. The fiber spatial irradiance distribution at 510 of a cylindrical fiber 506 is typically non-uniform, resulting on a non-uniform target spatial irradiance distribution at the target 508. This is not ideal for PIT and PDT application where a constant, uniform spatial irradiance distribution is required over the whole treatment area target 508.

Referring to FIG. 38A, the typical prior art addresses the issue of the non-uniform target spatial irradiance distribution at the target 508 as shown in FIG. 37C by including a mode mixing section 520 in the fiber 506 at a predetermined distanced location prior to the lens component 504. The effect of the mode mixing section 520 is to convert the non-uniform cross sectional spatial irradiance distribution at 510, as shown in FIG. 38B, to the significantly more uniform cross sectional spatial irradiance distribution at 514, as shown in FIG. 38C. Therefore, as shown in FIG. 38D, the target spatial irradiance distribution created by the lens component 504 at the target 508 will have a spatial irradiance distribution that is also more uniform.

The typical prior art mode mixing section 520 not only produces a more uniform fiber spatial irradiance distribution but it also creates a more uniform angular intensity distribution at the output of the fiber 506. However, when using a projection lens 504 to illuminate a target 508 as shown in FIG. 38A, the angular intensity distribution is not as important as the spatial irradiance distribution. This because the image formed by the projection lens 504 is essentially mapping all the light from one location in the fiber 506 to a location on the target 508, regardless of emission angle.

As discussed above, the mode mixing section 520 found in the prior art can be constructed of a serpentine section of one or more tight radius bends as shown in FIGS. 39A-39B, a coiled section of tight radius loops as shown in FIG. 39C, or a section with multiple turns of a tight radius helix as shown in FIG. 39D. Other art-disclosed embodiments of the mode mixing section 520 may also be used (e.g., alternating sections of graded and step index fibers, etc.). However, all these techniques suffer from a significant drawback, they create good mode mixing at the expense of creating high losses in the mode mixing section 520. In one exemplary prior art embodiment, the configuration in FIG. 38A is identical to the configuration in FIG. 37A with the addition of a mode mixing section 520 formed as shown in FIG. 39A with 7.5 mm radius bends. This embodiment exhibits a loss of −2.32 dB, requiring 3.25 Watts of input power to generate the irradiance distribution at the target shown in FIG. 38D.

At worst, these losses mean enough power leaks out of the fiber 506 to heat up the mode mixing section 520, resulting in catastrophic failure of the diffuser 500 and even presenting a safety concern to the operator and the patient. More subtle drawbacks are that the losses incurred by these types of mode mixer sections 520 tend to vary from device to device, making it hard to produce a consistent product and making it hard to calibrate the output from the pairing of a single device with a different light source.

Note that the lens component 504 may be comprised of a combination of one or more of optical elements including spherical, aspherical, graded index and diffractive elements. In the typical prior art, the fiber 506 and lens 504 are often part of a disposable assembly and the lens component 504 tends to have a small diameter.

Referring to FIG. 40A, this creates a condition where the beam of light 502 emerging from the lens component 504 is diverging. The diverging nature of the typical projection lens 504 results in different beam sizes at target position locations 516, 508 and 518 located at stand-off distance 520, 512 and 522 respectively in FIG. 40A. As the target is moved from position 516, past 508, ending at 518, the total power in the resulting beam is the same. However, as shown in the target spatial irradiance distributions in FIG. 40B, the size of the irradiance distribution on the target locations gets larger with distance while the value of the irradiance drops. This is not ideal, as the magnitude of irradiance of the beam (power/area) drops as a function of distance from the output face of the lens component 504 while the area illuminated increases, resulting in only a narrow range of standoff values where the irradiance meets the desired treatment values.

BRIEF DESCRIPTION OF THE DRAWINGS

The features and inventive aspects of the present invention will become more apparent upon reading the following detailed description, claims, and drawings, of which the following is a brief description:

FIG. 23 is a longitudinal cross-sectional view of the light diffusing section of a non-circular core fiber exemplary embodiment accordingly to the present invention;

FIG. 24 is a longitudinal cross-sectional view of the light diffusing section of a non-circular core fiber exemplary embodiment accordingly to the present invention;

FIG. 25 is a longitudinal cross-sectional view of the light diffusing section of a non-circular core fiber exemplary embodiment accordingly to the present invention;

FIG. 26 is a longitudinal cross-sectional view of the light diffusing section of a non-circular core fiber exemplary embodiment accordingly to the present invention;

FIG. 29 is a vertical cross-sectional view of a square shaped core fiber exemplary embodiment with the projected paths of its skew and meridional rays;

FIG. 30 is a vertical cross-sectional view of a circular shaped core fiber exemplary embodiment with the projected paths of its skew and meridional rays;

FIG. 31 is a graphical depiction of an exemplary cylindrical light diffusing device according to the present invention;

FIG. 40A is a graphical depiction of a prior art frontal light diffusing device shown with the targeted treatment area at various standoff distances (520, 512, 522);

FIG. 41A is a graphical depiction of an exemplary embodiment of a frontal light diffusing device according to the present invention;

DESCRIPTION OF THE PREFERRED EMBODIMENT

Figure 4:
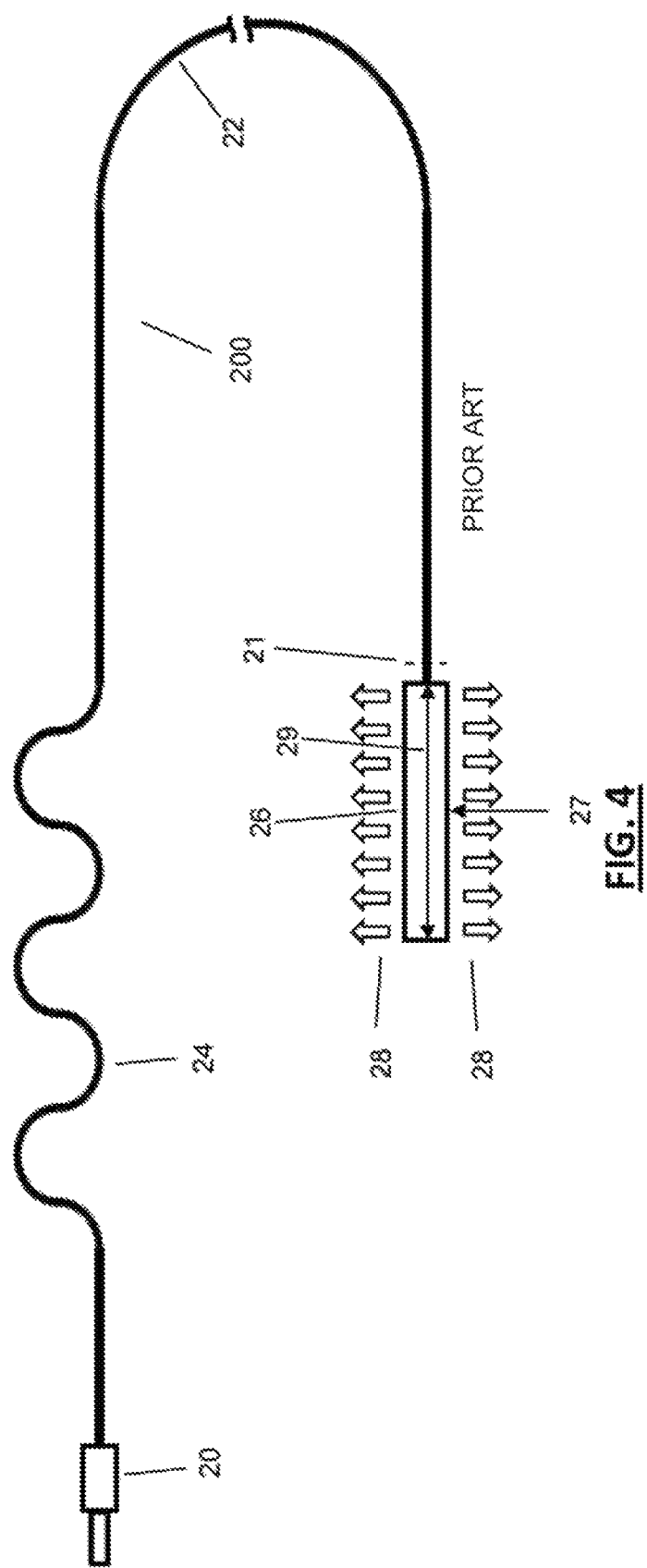
FIG. 4 is a graphical depiction of a prior art exemplary cylindrical light diffusing device that utilizes a mode mixer.

I. A Light Diffusing Device Providing a "Top Hat" Core Irradiance Distribution without a Conventional Mode Mixer Referring to FIGS. 9-26, the present invention provides a light diffusing device 300 having a non-circular core fiber 302 that provides a "top hat" core irradiance distribution (i.e., optimal core irradiance distribution) without the necessity of using a mode mixer (e.g., 24 shown in FIG. 4). The light diffusing device 300 of the present invention can emits irradiance in a radially symmetric longitudinally "top hat" diffusing irradiance distribution (i.e., optimal diffusing irradiance distribution) without the necessity of using the above-described known light diffusers and/or diffusing sections.

Figure 9:
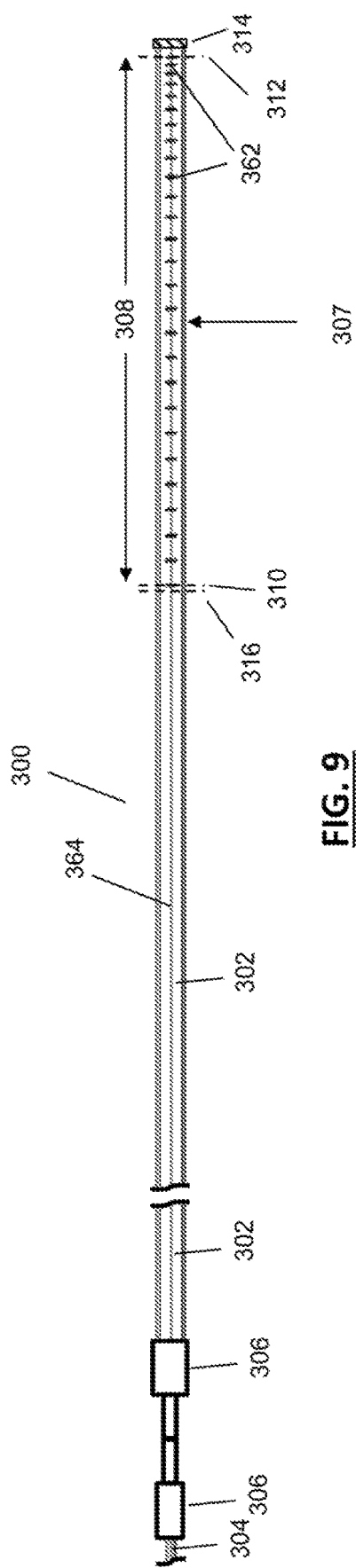
FIG. 9 is a graphical depiction of a cylindrical light diffusing device according to the present invention.
Figure 11:
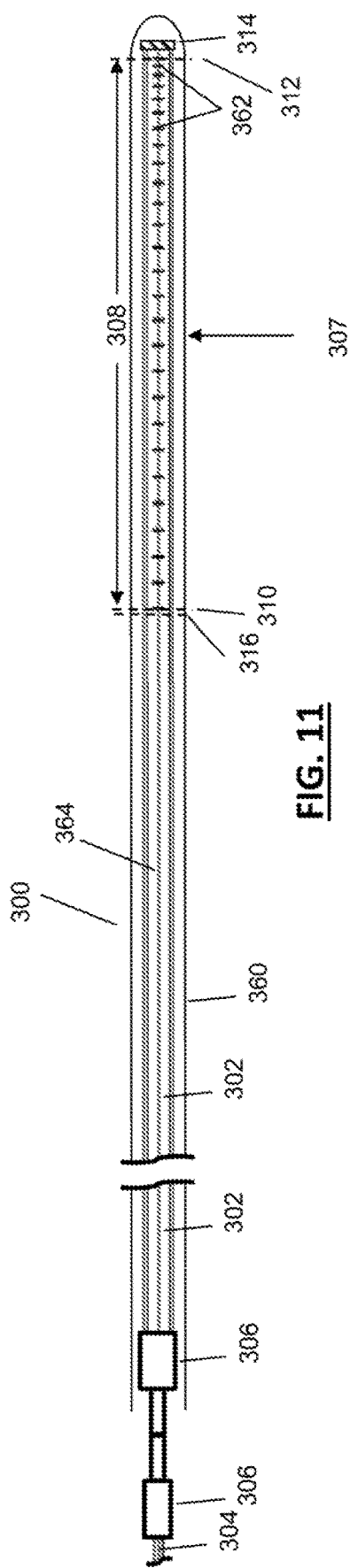
FIG. 11 is a graphical depiction of another embodiment of a cylindrical light diffusing device according to the present invention.

Referring to FIGS. 9 and 11, the device 300 further includes a lead-in optical fiber 304 and at least one optical connector 306. During operation, one end of the lead-in optical fiber 304 is in light communication to a light source (not shown) while the other end of the lead-in optical fiber 304 is in light communication with the proximal end of the non-circular core fiber 302 through the at least one optical connector 306 as shown in FIGS. 9 and 11. The non-circular core fiber 302 further includes a light diffusing section 308 having a diffusing proximal end 310 and a diffusing distal end 312.

In the exemplary embodiments shown in FIGS. 9 and 11, the light diffusing section 308 is located near the distal end of the non-circular core fiber 302. Furthermore, the non-circular core fiber 302 may optionally include a light blocking means 314 (e.g., physical cap, coating such as aluminum deposition, or the like) preventing superficial or frontal light emission from the distal end of the non-circular core fiber 302. In one embodiment, the light blocking means 314 is a mirror that turns light around and reuses it while avoiding over illuminating the treatment area. It provides a highly efficient light diffusing device because only about 6% of launch light couples back into the lead-in optical fiber 304.

In one embodiment, the lead-in optical fiber 304 is connected to the light source via an additional optical connector 306. The lead-in optical fiber 304 can be any conventional optical fiber including but not limited to the optical fiber (12, 22) described above. The at least one optical connector 306 connects and allows the lead-in optical fiber 304 to be in light communication with the non-circular core fiber 302 during operation. An alternative to the at least one optical connector 306 is a conventional glue joint or fusion joint between the lead-in optical fiber 304 and the non-circular core fiber 302. Furthermore and in an alternative exemplary embodiment, the non-circular core fiber 302 actually also serves as the lead-in optical fiber 304 (resulting in a single optical fiber) and is connected to a light source via the at least one optical connector 306, a glue/fusion joint, or other conventional connection means. The at least one optical connector 306 can be any art-disclosed optical connector (e.g., SMA connectors or the like).

Figure 15:
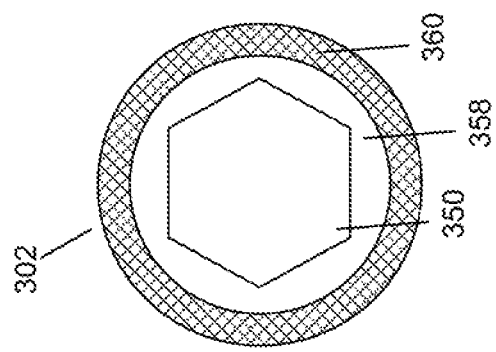
FIG. 15 is a vertical cross-sectional view of a non-circular core fiber exemplary embodiment accordingly to the present invention at a location right before the diffusing proximate end of the light diffusing section.
Figure 18:
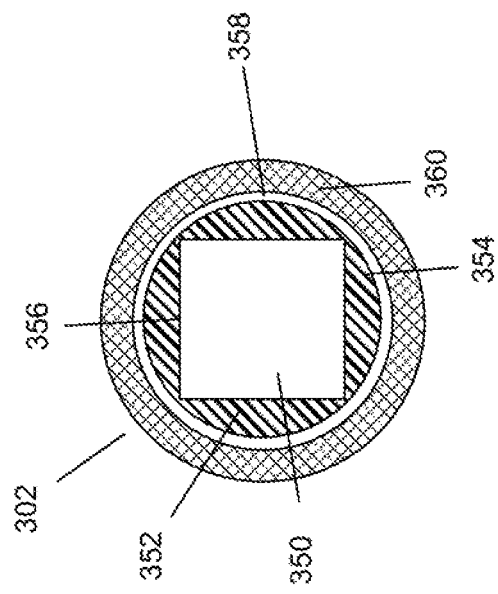
FIG. 18 is a vertical cross-sectional view of a non-circular core fiber exemplary embodiment accordingly to the present invention at a location right before the diffusing proximate end of the light diffusing section.
Figure 17:
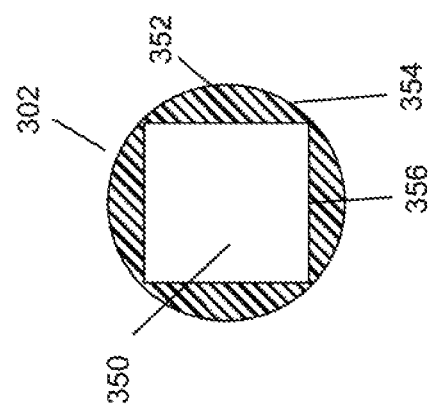
FIG. 17 is a vertical cross-sectional view of a non-circular core fiber exemplary embodiment accordingly to the present invention at a location right before the diffusing proximate end of the light diffusing section.
Figure 16:
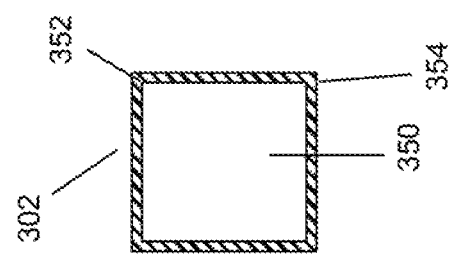
FIG. 16 is a vertical cross-sectional view of a non-circular core fiber exemplary embodiment accordingly to the present invention at a location right before the diffusing proximate end of the light diffusing section.
Figure 22:
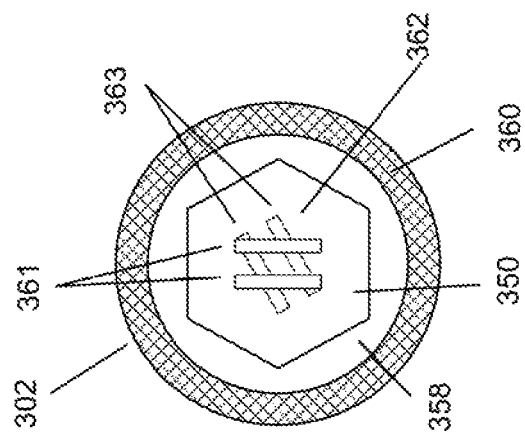
FIG. 22 is a vertical cross-sectional view of a non-circular core fiber exemplary embodiment accordingly to the present invention at a location with internal scattering features of the light diffusing section with another set of internal scattering feature superimposed.

FIGS. 13-18 each shows a vertical (i.e., latitudinal) cross-sectional view of the non-circular core fiber 302 at location 316, which is right before the diffusing proximate end 310 of the light diffusing section 308 (see FIGS. 9 and 11). FIGS. 10, 12 and 19-22 each shows a vertical cross-sectional view of the diffusing distal end 312 of the light diffusing section 308 as shown in FIGS. 9 and 11. The non-circular core fiber 302 includes a fiber core 350. The non-circular core fiber 302 may optionally include a cladding 352 as shown in FIGS. 10, 12-14 and 16-18. The fiber core 350 has a non-circular geometry such as hexagon (as shown in FIGS. 10 and 12-15), square (as shown in FIGS. 16-18), rectangle, triangle, octagon, other regular polygons and non-regular polygons. Accordingly, there is a wide range of potential non-circular core shapes that can achieve homogeneous irradiance inside the core. Some shape characteristics make a shape particularly well suited for the present invention. Although radial symmetry is not required, it does provide the benefits of ease of manufacture and promoting radially symmetric output irradiance pattern. The inclusion of inflection points in the cross section profile where the tangent of the shape changes rapidly encourages better mixing by sending adjacent rays in different directions. The inclusion of facets also promotes better mixing by avoiding self-focusing behavior. Avoiding re-entrant geometry aides in manufacture and avoids physically weak structures. These shape characteristics combined tend to encourage the use of regular polygon shapes as the basis for the non-circular core geometry. It should also be noted that a core with a helical or twisted shape could also be of interest for generating spatially homogeneous irradiance in the core.

Figure 12:
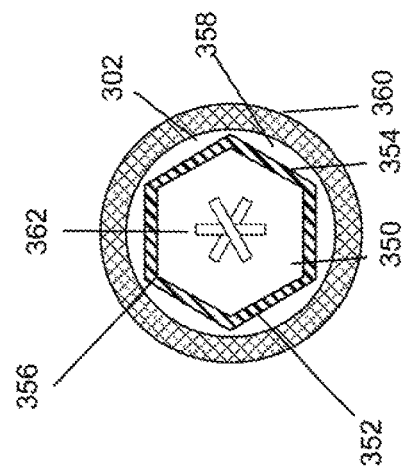
FIG. 12 is a vertical cross-sectional view of a non-circular core fiber exemplary embodiment accordingly to the present invention at a location right before the diffusing proximate end of the light diffusing section.
Figure 13:
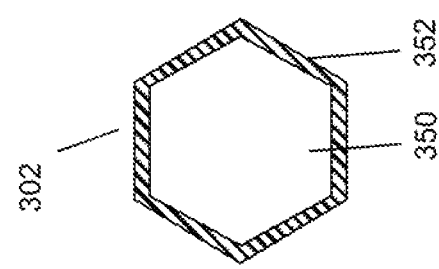
FIG. 13 is a vertical cross-sectional view of a non-circular core fiber exemplary embodiment accordingly to the present invention at a location right before the diffusing proximate end of the light diffusing section.

The cladding 352 may have the same non-circular vertical (i.e., latitudinal) cross sectional geometry as the fiber core 350 (see e.g., FIGS. 12, 13, and 16). Alternatively, the cladding 352 may have a circular exterior surface geometry 354 with an interior surface geometry 356 that has the same general shape as the fiber core 350 (see e.g., FIGS. 10, 14, 17 and 18).

Referring to FIGS. 15, 19-22, in some exemplary embodiments of the present invention, the cladding 352 does not exist but is replaced with an enclosed open cavity or environment (e.g., air) 358 between the fiber core 350 and a covering 360 that is concentric with the fiber core 350 and radially envelopes (but does not tightly cladded) the fiber core 350. The covering 360 can be any suitable art-disclosed polymeric material (e.g., Pebax®) and is generally circular in shape as shown in FIGS. 11, 12, 15, 18-22. The covering 360 offers additional protection for the non-circular core fiber 302. The covering 360 can be clear or translucent. If clear, the covering 360 does not provide any light scattering thus no extra losses of light. If translucent, internal scattering by the covering 360 can assist in improving the uniformity of the diffusing irradiance distribution. However, too much internal scattering by the covering 360 can cause excess losses of light due to absorption.

As shown in FIGS. 12 and 18, it is possible to mix and match the fiber core 350 and the cladding 352 in different vertical cross sectional geometries and combined them with either the enclosed open cavity 358 and/or the covering 360. For example and referring to FIG. 18, a vertical cross sectional view of the non-circular core fiber 302 shows its fiber core 350 has a square geometry. The interior surface geometry 356 of its cladding 352 matched this square geometry while the exterior surface geometry 354 of its cladding 352 is circular in shape. The non-circular core fiber 302 further includes the enclosed open cavity 358, which is sandwiched between the cladding 352 and the covering 360. The covering 360 has a circular geometry.

Figure 14:
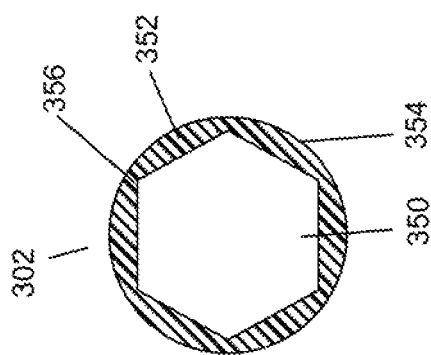
FIG. 14 is a vertical cross-sectional view of a non-circular core fiber exemplary embodiment accordingly to the present invention at a location right before the diffusing proximate end of the light diffusing section.

In one exemplary embodiment of the device 300 and referring to FIGS. 9 and 14, the fiber core 350 of the non-circular core fiber 302 is constructed out of poly (methyl methacrylate) ("PMMA") with a hexagonal geometry in a circumscribed ø660 μm diameter circle. The fiber core 350 is clad by the cladding 352 with an interior surface geometry 356 that has the same hexagonal geometry as the fiber core 350. However, the exterior surface geometry 354 of the cladding 352 is circular. The cladding 352 is constructed of a silicone with an ø740 μm OD. The lead-in fiber 304 of the device 300 has a 200 μm OD glass core and a 230 μm OD cladding. The length of the non-circular core fiber 302 is 30 cm. During operation, the core optical fiber 302 is filled with laser light having an angular distribution of a NA of 0.22. It should be noted that other embodiments could include different materials for both the core and cladding, including utilizing various transparent or translucent glasses and polymers. If the total length of the diffuser is short, then absorbance is not of primary concern, but the materials should not be opaque at the wavelengths of interest. For example, if the diffuser is to be used to provide UV illumination then a silica core light guide is appropriate, whereas use of mid wave IR light would encourage the use of a fluorite or silver halide glass. A wide range of injection moldable polymer materials are appropriate for visible and near IR applications, including but not limited to PMMA, poly carbonate (PC) and polystyrene (PS). Various castable materials including epoxies and silicones are also of interest. In all cases, care should be utilized to ensure the materials could handle the required amount of optical power without ill effects, such as melting or crazing.

Figure 5:
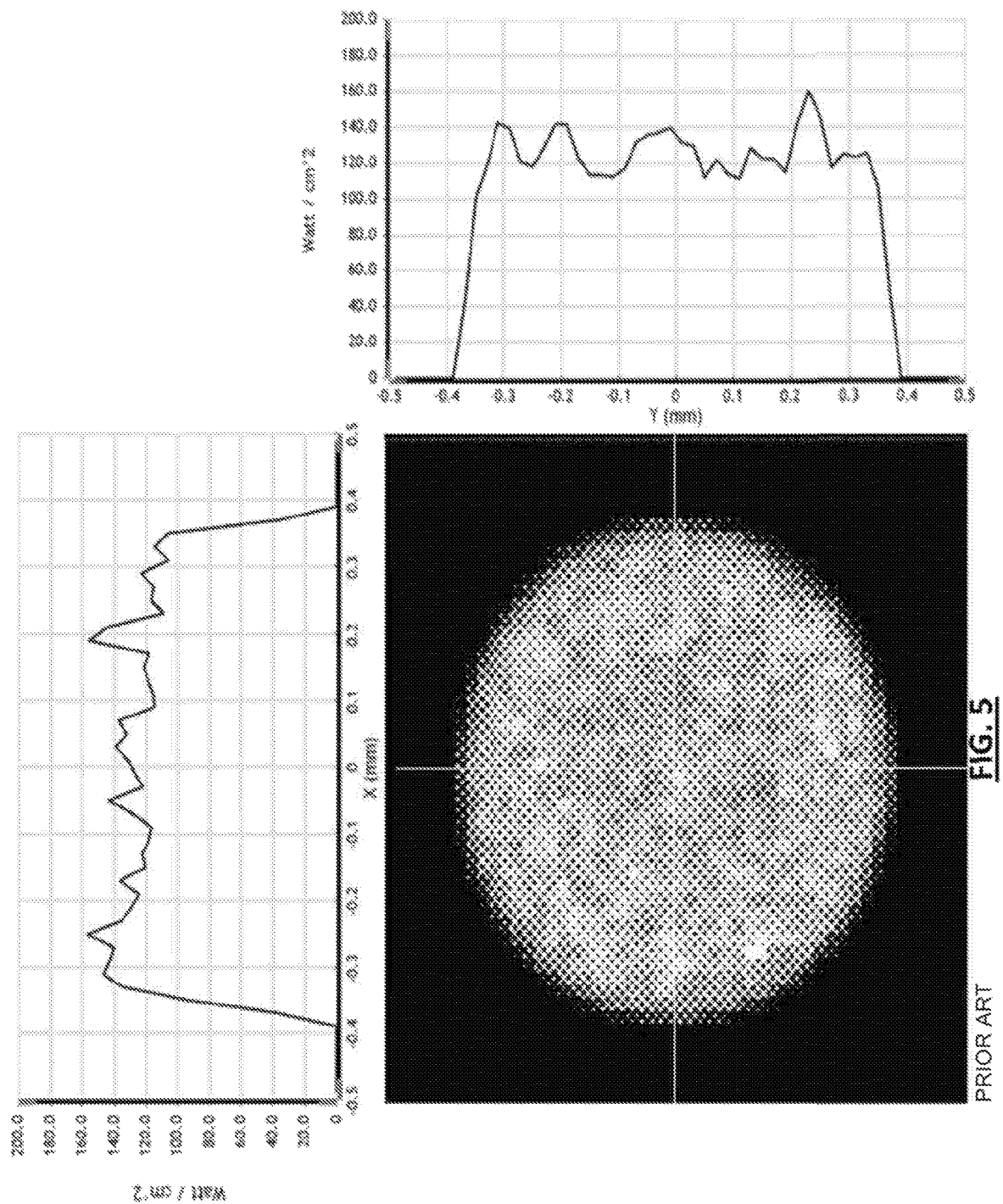
FIG. 5 is a map of the irradiance at a vertical cross-section of the optical fiber of the cylindrical light diffusing device of FIG. 3 and its associated irradiance distribution graphs.
Figure 27:
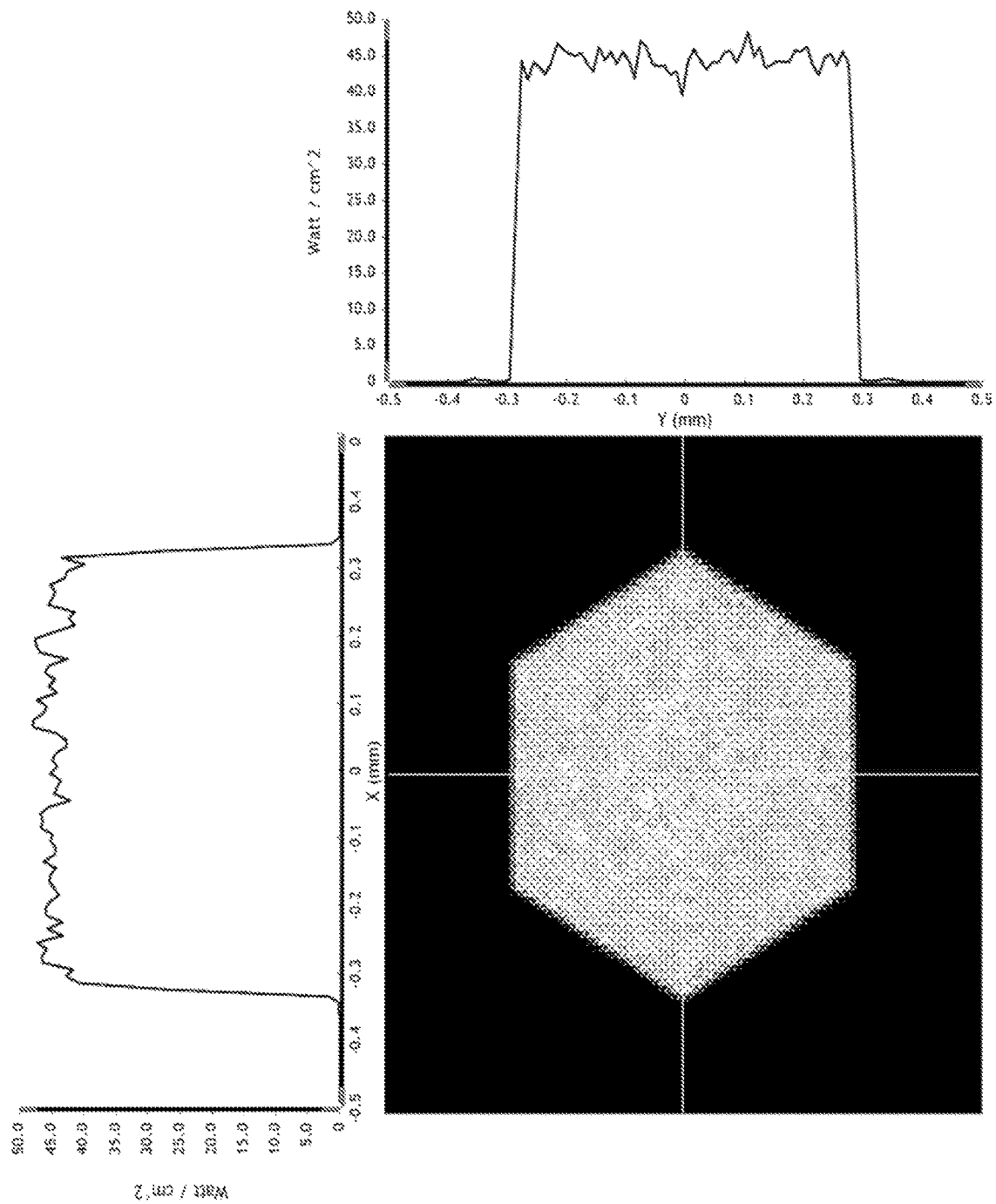
FIG. 27 is a map of the irradiance at a vertical cross-section of the optical fiber of the cylindrical light diffusing device of FIGS. 9 and 14 and its associated irradiance distribution graphs.

FIG. 27 shows a map of the irradiance at the vertical cross-section (shown as "316" in FIG. 9) through the fiber core 350 taken just before the diffusing proximal end 310. The light source used is a 690 nm laser with 0.125 Watt launch power and this power was adjusted until the irradiance measured at the center 307 of the longitudinally length of the light diffusing section 308 was 150 mW/cm². This measurement is taken 0.75 mm from the central axis of the stated location of the light diffusing section 308. The total length of optical fiber (combination of the lead-in fiber 304 and the non-circular core fiber 302) from the light source leading up to this location 316 is 2 meter long. The associated irradiance distribution graphs shown in FIG. 27 taken from vertical and horizontal cross sections through the center of the map of the irradiance show the same "top hat" core irradiance distribution as the above-discussed conventional cylindrical light diffusing device 200 (shown in FIG. 5), which requires a mode mixer (24). This "top hat" core irradiance distribution indicates a high degree of uniformity of the irradiance distribution in the fiber core 350 (i.e., optimal core irradiance distribution). "Top hat" core irradiance distribution and/or optimal core irradiance distribution shall be defined hereinafter in this Specification as having all irradiance of a cross-section of the fiber core 350 to be within at least +/−20% of the average irradiance of the cross-section of the fiber core 350, indicating a high degree of uniformity of the irradiance distribution in the core of the fiber 22. In some exemplary embodiments, the at least +/−20% value can be further reduced to +/−15% range, or even +/−10% range.

The examination of two types of rays that can propagate in a perfectly symmetrical cylindrical light guide may assist in understanding how the non-circular core fiber 302 of the present invention can provide a "top hat" core irradiance distribution in the fiber core 350. It is possible for light to propagate forward as "skew rays" that spiral around the outer edge of the fiber core 350 without ever crossing through the center portion of the fiber core 350. This is depicted in FIG. 30 which shows a vertical cross-sectional view of a circular shaped core fiber 301 where the projected path of a propagating skew ray 366 that always stays near the edge of the fiber core 351. It is also possible to have meridional rays 368 with paths that lie on a plane so that rays that start on the central axis of the light guide always cross back though the central axis of the fiber core 351. In comparison and referring to FIG. 29, which shows a vertical cross-sectional view of a square shaped non-circular core fiber 302 with the projected path of similar propagating rays. The skew ray 370 still propagates without crossing the central axis of the fiber core 350, but now its path is such that its energy can at some locations be found near the edges of the fiber core 350 while in other locations it can be found closer the center of the fiber core 350. A meridional ray 372 that starts on the central axis of the fiber core 350 can have a path that samples much of the area of the fiber core 350 without ever crossing the axis again. These two examples demonstrate how introducing a large set of rays with a range of different launch angles into a non-circular core fiber 302 can yield a "top hat" core irradiance distribution after a short propagation length that corresponds to only a few internal reflections.

Our study indicates that replacing the non-circular core fiber 302 shown in FIG. 14 with any of the above-discussed different embodiments of the non-circular core fiber 302 would still allow the device 300 to provide the desired "top hat" core irradiance distribution (e.g., FIGS. 13-18). For example, the fiber core 350 of FIG. 13 is same as the fiber core 350 shown in FIG. 14. They both are constructed out of PMMA with a hexagonal geometry in a circumscribed ø660 μm diameter circle.

The non-circular core fiber 302 of FIG. 13 differs from the core fiber of FIG. 14 because the cladding 352 of FIG. 13 has a hexagonal geometry. The cladding 352 of FIG. 13 is constructed of a fluorinated polymer in a circumscribed ø740 um diameter circle.

In another exemplary embodiment and referring to FIG. 15, the fiber core 350 has the same geometry and dimensions as the fiber core of FIG. 14 except that it is constructed out of polystyrene instead of PMMA. However, the non-circular core fiber 302 of FIG. 15 does not have the cladding 352. Instead, it (302) further includes the enclosed open cavity 358 and the covering 360. The covering 360 is constructed of a translucent Pebax® resin with an ø1000 μm OD and an ø900 μm inner diameter ("ID"). In this exemplary embodiment, the trapped air contained in open cavity 358 acts as a cladding to ensure the light is contained within the fiber core 350.

The exemplary embodiments shown in FIGS. 16-17 use the same fiber core 350 constructed out of PMMA with a 500 μm×500 μm square geometry. The non-circular core fiber 302 of FIG. 16 has a cladding 352 constructed out of fluorinated polymer with a 540 μm×540 μm square geometry. The non-circular core fiber 302 of FIG. 17 has a different cladding 352 as it has a square interior surface geometry 356 and a circular exterior surface geometry 354. The cladding 352 is constructed of a silicone with an ø740 μm diameter OD.

In another exemplary embodiment and referring to FIG. 18, the fiber core 350 has the same geometry and dimensions as the fiber core 350 of FIG. 17 except that it is constructed out of polystyrene instead of PMMA. Both have the same cladding 352. However, the non-circular core fiber 302 of FIG. 18 further includes the enclosed open cavity 358 and the covering 360. The covering 360 is constructed of a translucent Pebax® resin with an ø1000 µm OD and an ø900 µm ID.

In yet another exemplary embodiment and referring to FIG. 12, the non-circular core fiber 302 is a combination of the core fiber shown in FIG. 13 plus the enclosed open cavity 358 and the covering 360. The covering 360 is constructed of a translucent Pebax® resin with an ø1000 µm OD and an ø900 µm ID.

As discussed above, the non-circular core fiber 302 of the present invention with its variety of shapes, materials, cladding (352), and covering (360) can provide "top hat" core irradiance distribution without needing a mode mixer thus providing a less expensive and sturdier light diffusing device (300). The non-circular core fiber 302 of the present invention can be used in conjunction with one of the above-described conventional lighting diffusers or diffusing sections to provide "top hat" diffusing irradiance distribution.

II. Cylindrical Light Diffusing Device Providing a "Top Hat" Diffusing Irradiance Distribution In order for the device 300 to provide a "top hat" diffusing irradiance distribution without using such a conventional light diffuser or diffusing section, the device 300 must include internal (i.e., not reaching the exterior surface of the fiber core 350) scattering features 362, preferably inscribed or written by laser, within the light diffusing section 308 as shown in FIGS. 9 and 11.

The "top hat" diffusing irradiance distribution is defined in this Specification as having a longitudinal variation of the out-coupled irradiance to be less than +/−20% of the average ("$I_o$") optical irradiance for a cylindrical diffuser in terms of the radially emitted irradiance distribution (see e.g., FIG. 6), indicating a high degree of uniformity. In some exemplary embodiments, the at least +/−20% value can be further reduced to +/−15% range, or even +/−10% range.

Figure 10:
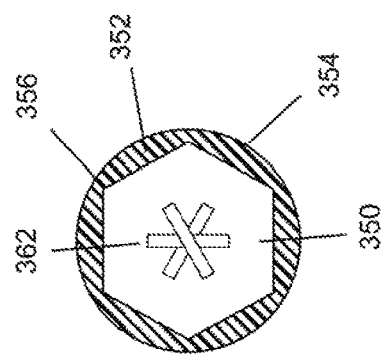
FIG. 10 is a vertical cross-sectional view of a non-circular core fiber exemplary embodiment accordingly to the present invention at a location right before the diffusing proximate end of the light diffusing section.
Figure 21:
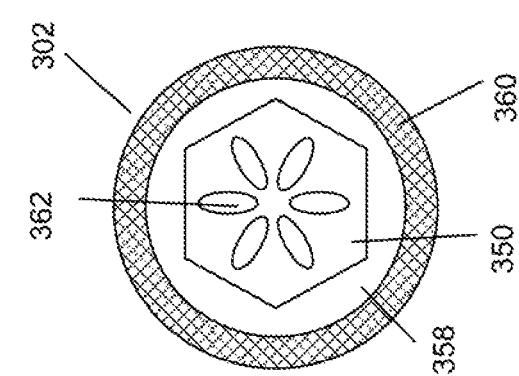
FIG. 21 is a vertical cross-sectional view of a non-circular core fiber exemplary embodiment accordingly to the present invention at a location with an internal scattering feature of the light diffusing section.
Figure 20:
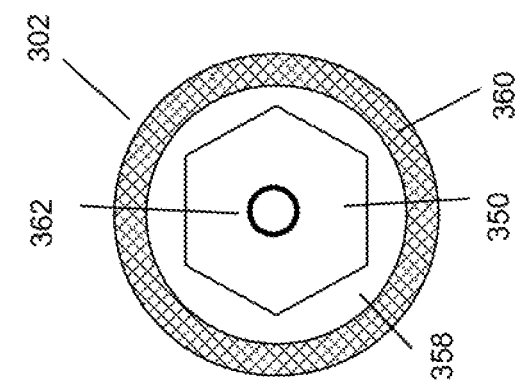
FIG. 20 is a vertical cross-sectional view of a non-circular core fiber exemplary embodiment accordingly to the present invention at a location with an internal scattering feature of the light diffusing section.
Figure 19:
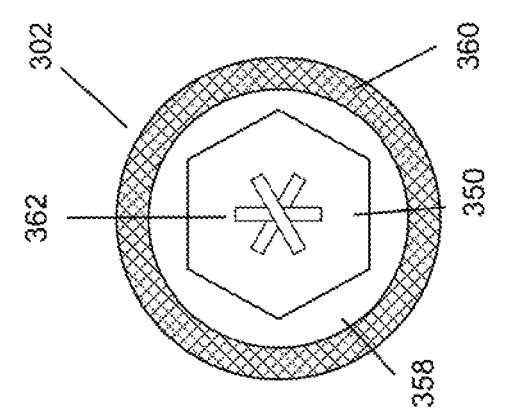
FIG. 19 is a vertical cross-sectional view of a non-circular core fiber exemplary embodiment accordingly to the present invention at a location with an internal scattering feature of the light diffusing section.

The internal scattering features 362 generally begin at the diffusing proximal end 310 and end at the diffusing distal end 312. The features 362 can be in a variety of shapes and patterns as shown in FIGS. 10, 12, 19-22. FIGS. 10, 12, 19-22 show a vertical (i.e., latitudinal) cross-sectional view of the diffusing distal end 312 of the light diffusing section 308. For example, the features 362 can be (i) three cylinders oriented around the central axis of the fiber core 350 at 60° increments as shown in FIGS. 10, 12 and 19 (ii) a single line of spheres concentric to the central axis of the fiber core 350 as shown in FIG. 20; (iii) a symmetrical array of elliptical features (e.g., features that are elliptical or spherical) centered on radius around the central axis of the fiber core 350 at 60° increments as shown in FIG. 21 and distributed down a predetermined longitudinal length of the fiber core 350 in linear, nonlinear, spiral pattern, or pseudo random pattern; and (iv) a pair of parallel cylinders 361 where each cylinder of a pair are located at a predetermined distance from the central axis of the fiber core 350, with subsequent pairs of cylinders that are located at different longitudinal locations along the length of the light diffusing section 308 are oriented at different angles around the central axis of the fiber core 350, (e.g. the pair of parallel cylinders 363 are located at a different cross section of the fiber and are clocked at 60° relative to the pair 361). Please note that while the embodiments discussed herein use 60° increments, other predetermined patterns such may also be suitable such as, without limitations, 45°, 72°, 90°, 120°, 180° increments.

Each scattering feature 362 can be created by a suitable art-disclosed laser. For example, a focused, mode-locked 532 nm 10 pico-second laser pulse at 1.5 Watts average power can create the features 362 shown in FIG. 10, which are comprised of three cylinders, each approximately 27 µm in diameter and 270 µm in length oriented around the central axis of the fiber core 350 at 60° increments. In another example, a series of 520 nm 400 fempto-second laser pulses at 2.0 Watts average power focused through an objective lens with a numerical aperture of 0.4 can create the features 362 shown in FIG. 43 (discussed in more details below), each feature a sphere approximately 40 um in diameter centered around the central axis of the fiber core 350 at increments of 60°. Please note that while the embodiments discussed herein use 60° increments, other degree increments are also suitable such as 45°, 72°, 90°, 120°, 180°, etc.

The scattering characteristics of each of the features 362 are varied by material, geometry and processing. The proportion of light scattered per length or per feature 362 must increase as the density of light per length in the light diffusing section 308 decreases due to light being scattered out of the non-circular core fiber 302. This can be achieved by changing the number of features 362 per unit length or the size of the features 362 as a function of length. Depending on the amount of return light acceptable, linear increase in size may suffice but a non-linear increase in size vs length may be preferred. In another exemplary embodiment, the number of features 362 per unit length may increase while the size of the features 362 as a function of length may decrease. It should be noted that it is also possible for one skilled in the art to change the processing parameters in order to change the amount of scattering per feature 362.

When the internal scattering features 362 are distributed in the light diffusing section 308 along the central axis 364 of the non-circular fiber core 350 as shown in FIGS. 9 and 11, the light propagates down the light diffusing section 308 and there is constant mixing occurring in the light diffusing section 308 itself. As the light in the center of the fiber core 350 encounters the internal scattering features 362 and is scattered out of the light diffusing section 308, the light redistribution ensures the irradiance in the center of the fiber core 350 is replenished. This simplifies the challenge of finding a pattern of scattering features 362 to achieve a uniform emission pattern while allowing the scattering features 362 to be kept smaller and located towards the center of the light diffusing section 308, resulting in a potentially more physically robust device with better emission characteristics.

Referring to FIGS. 23-26, the feature 362 can also be longitudinally spaced in a variety of patterns. For example, the features 362 can be arranged longitudinally in a uniform linear manner concentric with the central axis 364 of the fiber core 350 as shown in FIG. 23. The features 362 can be arranged longitudinally in a non-uniform linear manner by changing the number of the features 362 per unit length as shown in FIG. 24. In FIG. 24, the number of features 362 per unit length increases going from the diffusing proximate end 310 to the diffusing distal end 312 of the light diffusing section 308. As discussed above and in the alternative, the number of features 362 per unit length may decrease going from the diffusing proximate end 310 to the diffusing distal end 312 of the light diffusing section 308 but size of the features 362 may increase going from the diffusing proximate end 310 to the diffusing distal end 312 of the light diffusing section 308.

Furthermore, the features 362 can be arranged longitudinally in a uniform linear manner with a linear increase in size as shown in FIG. 25. Finally, the features 362 can be arranged longitudinally in a uniform manner with a non-linear increase in size as shown in FIG. 26.

III. Frontal Light Diffusing Device Providing a "Top Hat" Spatial Irradiance Distribution Referring to FIG. 41A, the present invention provides a frontal light diffusing device 600 including a fiber optic connector 603, a cylindrical optical fiber section 602, a non-circular core fiber section 604, a fiber splice 605 joining the two fiber sections, and a lens component 606. During the operation of the device 600, the cylindrical optical fiber section 602 is in light communication with the non-circular core fiber section 604, and the non-circular core fiber section 604 is also in light communication with the lens component 606. The non-circular core fiber section 604 can have the same characteristics as the above-discussed non-circular core fiber 302 which provides a "top hat" core irradiance distribution (without the necessity of using a mode mixer) except that it does not include the optional light blocking means 314 discussed above. Please note the cross section can also vary down the longitudinal length of the non-circular core fiber section 604 to assist in creating a better mixing effect, e.g. there can be one or more regions of 604 where the outer dimension of the core increases and then decreases, or the core of 604 can have varying amounts of twist (i.e., rotation around the longitudinal axis of the fiber section 604) instead of a straight extrusion, or the non-circular profile of 604 can vary from one shape to another (e.g. hexagonal to square). The non-circular core fiber section 604 acts as a spatial mode mixer to cause several internal bounces of the propagating light so that there is little to no loss of propagating light.

As discussed below and in one exemplary embodiment, during operation, the cylindrical optical fiber section 602 has the non-uniform fiber spatial irradiance distribution of light shown in FIG. 41B as measured at cross section 608. The non-circular core fiber section 604 outputs the significantly more uniform mixed fiber spatial irradiance distribution shown FIG. 41C as measured at cross section 610. The target spatial irradiance distribution shown in FIG. 41D created by lens component 606 at the target cross section 614 is also more uniform. Accordingly, both the mixed spatial irradiance distribution measured at 610 and the target spatial irradiance distribution measured at 614 have the desired "top hat" spatial irradiance distribution. The "top hat" spatial irradiance distribution and/or optimal spatial irradiance distribution shall hereinafter be defined as having variation of the out-coupled spatial irradiance distribution be less than +/−20% of the average ("$I_0$") optical irradiance for a frontal diffuser in terms of the emitted irradiance distribution, indicating a high degree of uniformity of the spatial irradiance distribution at the relevant location (e.g., at 610 and/or at target 614). In some exemplary embodiments, the at least +/−20% value can be further reduced to +/−15% range, or even +/−10% range.

In the prior art, the mixing of propagation angles means that some rays of light that did propagate down the fiber core get perturbed into angles that exceed the critical angle of the fiber and are emitted, resulting in transmission loss and other unwanted effects like local heating of the surrounding materials. The non-circular core fiber section 604 does not change the angles such that they cannot propagate, they only re-arrange the paths of the rays while preserving the angle of each ray to the optical axis of the non-circular core fiber section 604. As discussed above, it is possible to create variations in the shape or size of the non-circular core fiber section 604 down the length of the mixing section so that controlled amounts of angular mixing can be included in the effect of the non-circular core fiber section 604, noting that any increased angular mixing will also be accompanied by incurring corresponding transmission losses.

In one alternative embodiment of the present invention, the non-circular core fiber section 604 can extend from the light source to the projection lens (e.g., 606) or, as shown in FIG. 41A, a short section 604 can be utilized after a cylindrical fiber section 602 and prior to the lens component 606. Note that if a section of cylindrical fiber 602 is used between the non-circular core fiber section 604 and the lens component 606, care should be utilized that it not be too long (e.g., less than 0.25 meters or the like) or the mixed spatial irradiance distribution measured prior to 606 can become non-uniform again.

As discussed above for the non-circular core fiber 302, the non-circular core fiber section 604 can be a separate piece of material that is connected using standard fiber optic connectors 605 or is can be permanently affixed to one end of the cylindrical fiber section 602 by glue or even melted into place by a fusion bonding technique. It is also possible to mold or emboss a non-cylindrical section 604 into an otherwise cylindrical section of fiber 602. Care should be taken to engineer the junction between the cylindrical fiber section 602 and the non-circular core fiber section 604 to minimized losses, e.g., matching sizes and maximum propagation angles.

Referring to FIG. 41A and in one exemplary embodiment of device 600, the cylindrical optical fiber section 602 is comprised of a core fiber constructed out of glass with a 600 μm OD core covered by a 630 μm OD cladding. It has numerical aperture (NA)=between 0.22 and 0.26. The non-circular fiber core section 604 is at least 50 mm in length and constructed out of glass with a hexagonal geometry of 600 μm ID, with a 680 μm OD cladding. The lens component 606 is comprised of a ¼ pitch, 1 mm diameter GRIN lens.

In one exemplary embodiment, the light source used is a 690 nm laser with 2.4 Watt launch power and this power was adjusted until the irradiance measured at the target 614 was 150 mW/cm$^2$ with a top hat distribution with a 42 mm internal diameter when measured with the stand-off (e.g. 616)=64 mm. This embodiment demonstrates low transmission losses of −0.36 dB. The total length of optical fiber (combination of the cylindrical optical fiber section 602 and the non-circular core fiber section 604) from the light source to the projection lens 606 is 2 meter long.

Figure 41B:
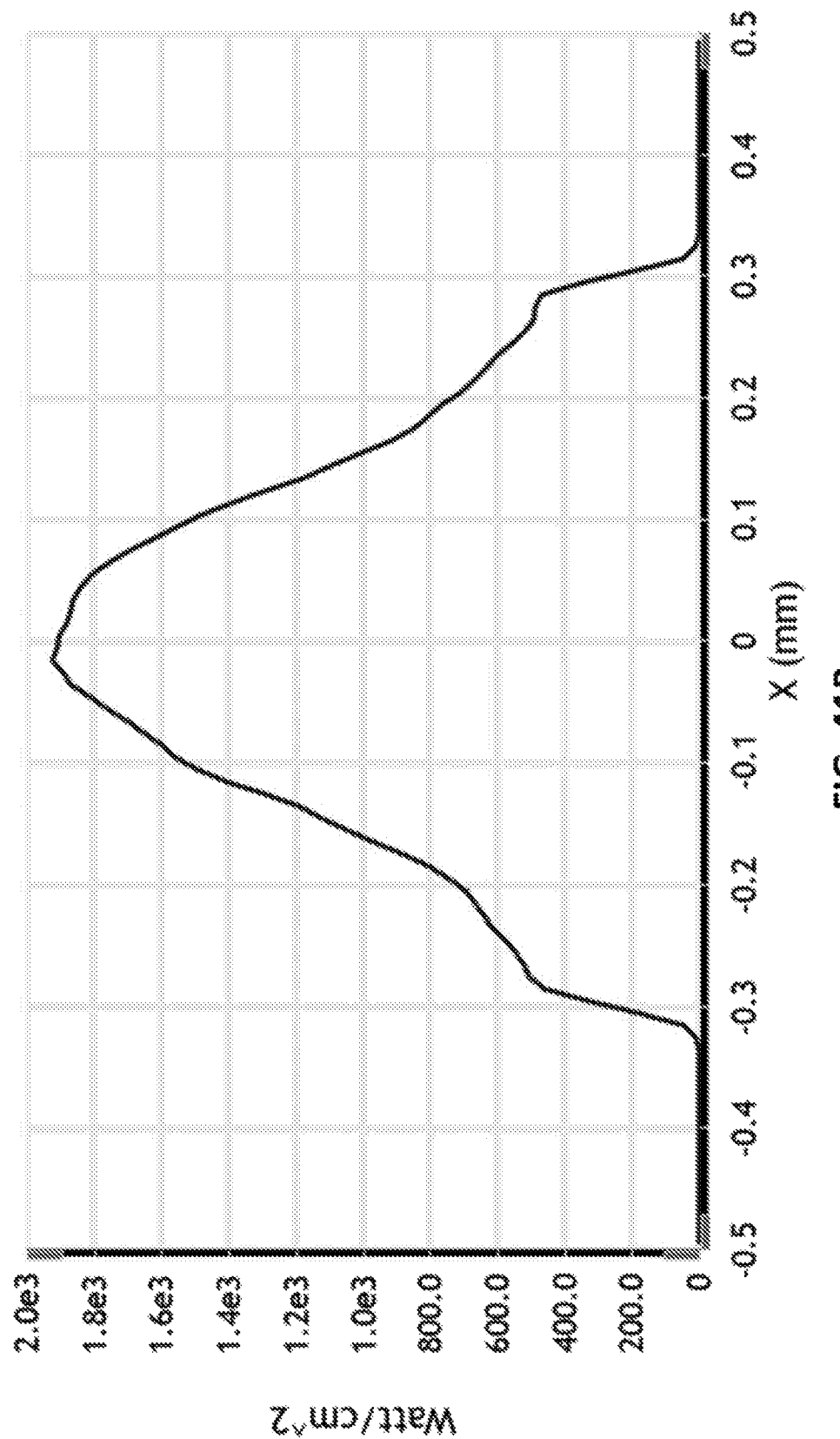
FIG. 41B is a graph of the spatial irradiance distribution along a vertical cross section (608) of the optical fiber of the frontal light diffusing device in FIG. 41A.
Figure 41C:
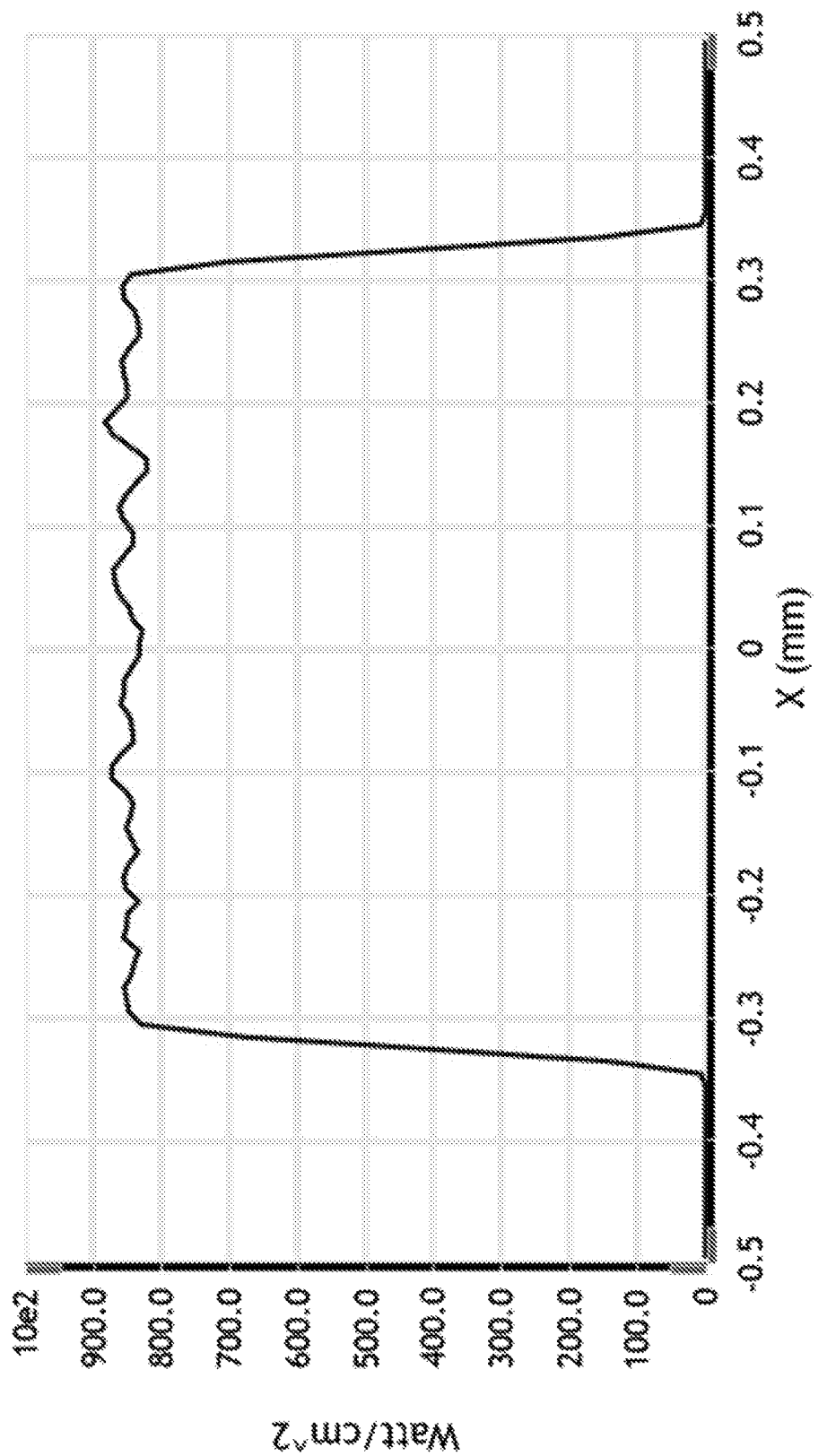
FIG. 41C is a graph of the spatial irradiance distribution along a vertical cross section (610) of the optical fiber of the frontal light diffusing device in FIG. 41A.
Figure 41D:
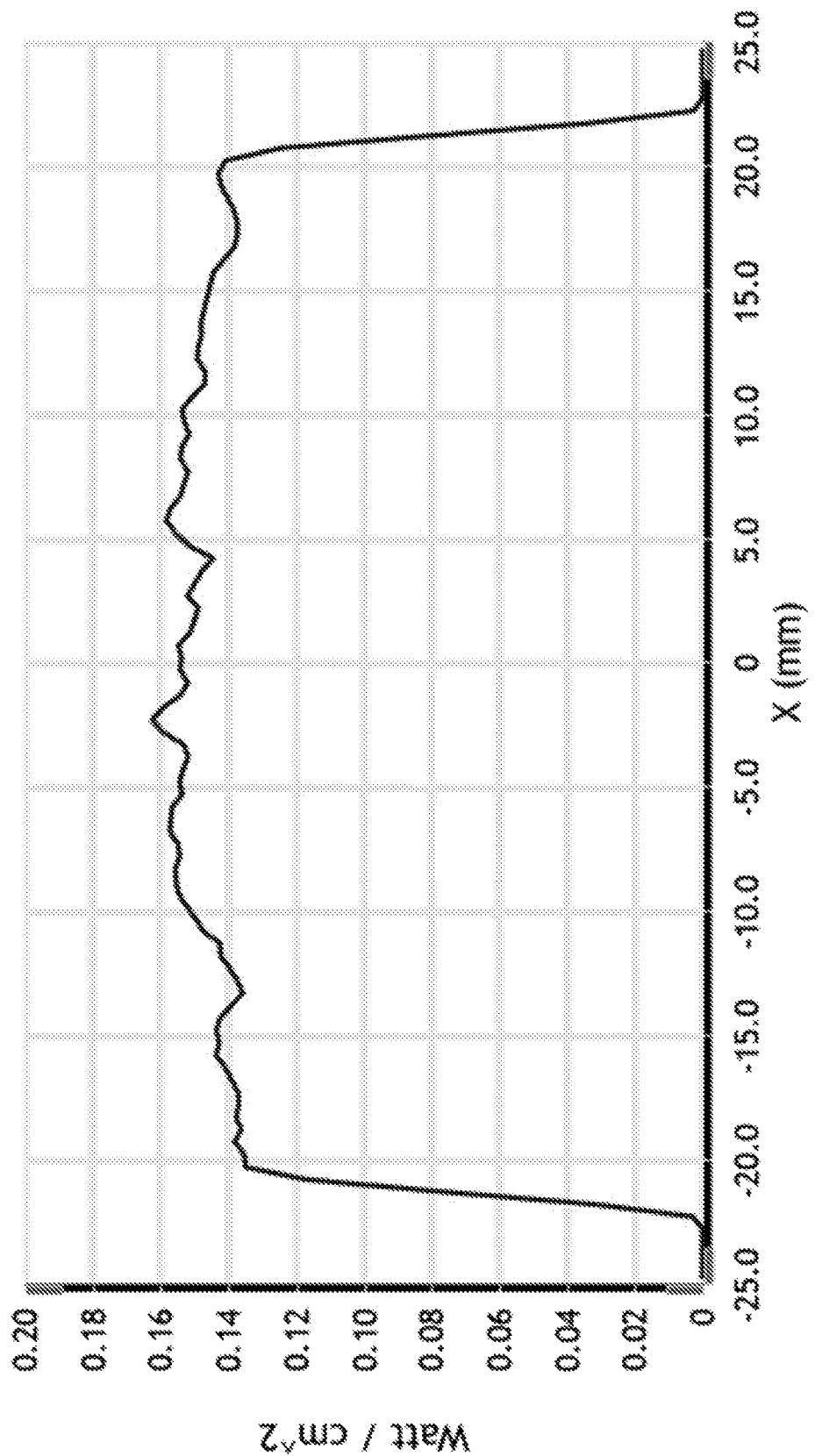
FIG. 41D is a graph of the spatial irradiance distribution along a vertical cross section (614) of the target by the frontal light diffusing device in FIG. 41A.

During operation, the cylindrical optical fiber section 602 has the non-uniform fiber spatial irradiance distribution of light shown in FIG. 41B as measured at cross section 608. The non-circular core fiber section 604 outputs the significantly more uniform mixed fiber spatial irradiance distribution shown FIG. 41C as measured at cross section 610. The target spatial irradiance distribution shown in FIG. 41D created by lens component 606 at the target cross section 614 is also more uniform. Accordingly, both the mixed spatial irradiance distribution measured at 610 and the target spatial irradiance distribution measured at 614 have the desired "top hat" spatial irradiance distribution.

Figure 40B:
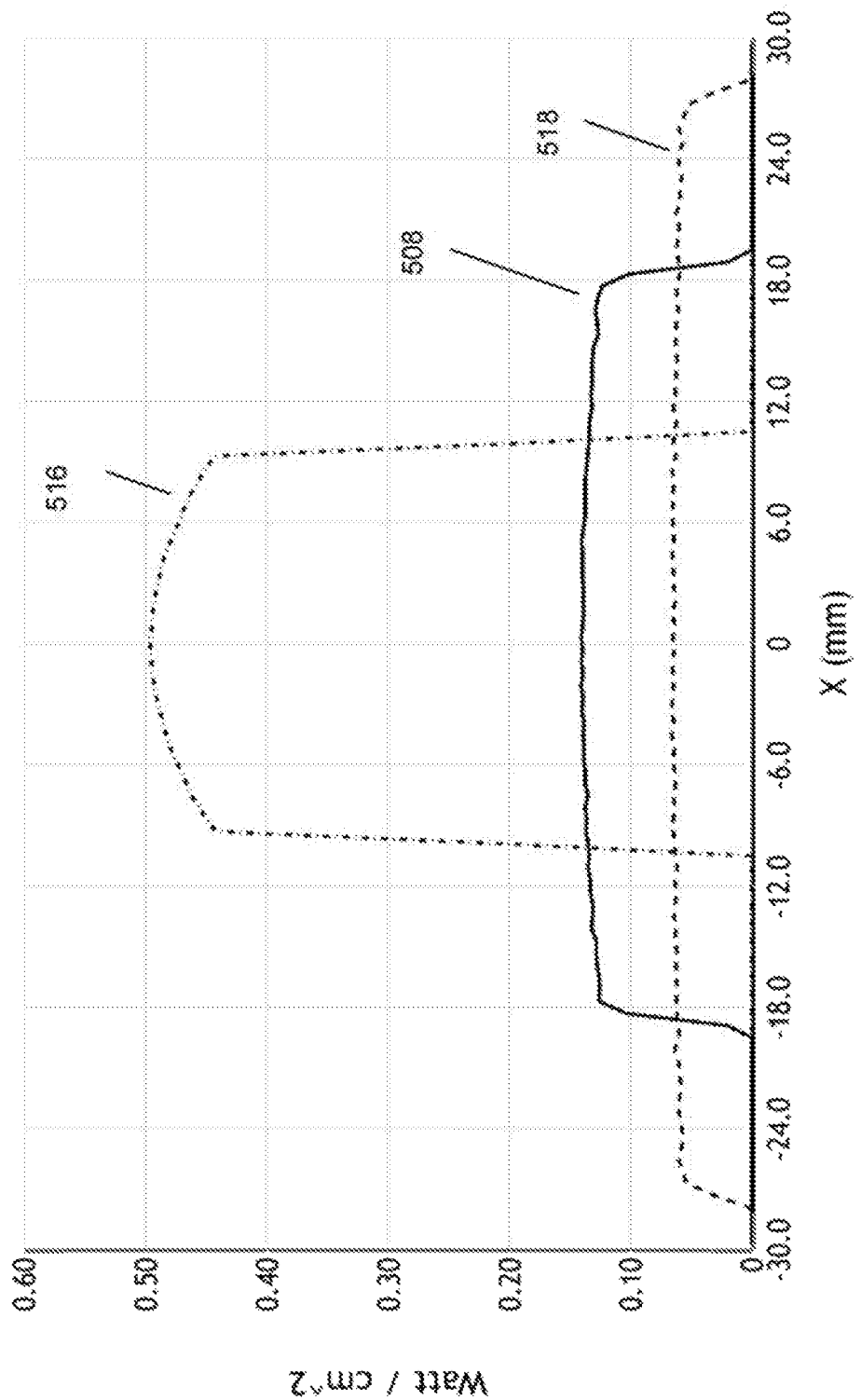
FIG. 40B is a graph of the spatial irradiance distributions along vertical cross sections (516, 508, 518) of the targeted treatment area at various standoff distances (520, 512, 522) by the frontal light diffusing device in FIG. 40A.

As shown in FIG. 40A and FIG. 40B, the prior art frontal illuminators have diverging beams. This forces the operator to hold the illuminator at a very specific standoff from the target zone for the duration of the treatment in order to achieve the desired irradiance levels. An ideal frontal illuminator would have the same irradiance on the target regardless of the standoff distance. Additionally, the ideal frontal illuminator would also allow the size and shape of the illumination pattern on the target to easily be adjusted.

Figure 42A:
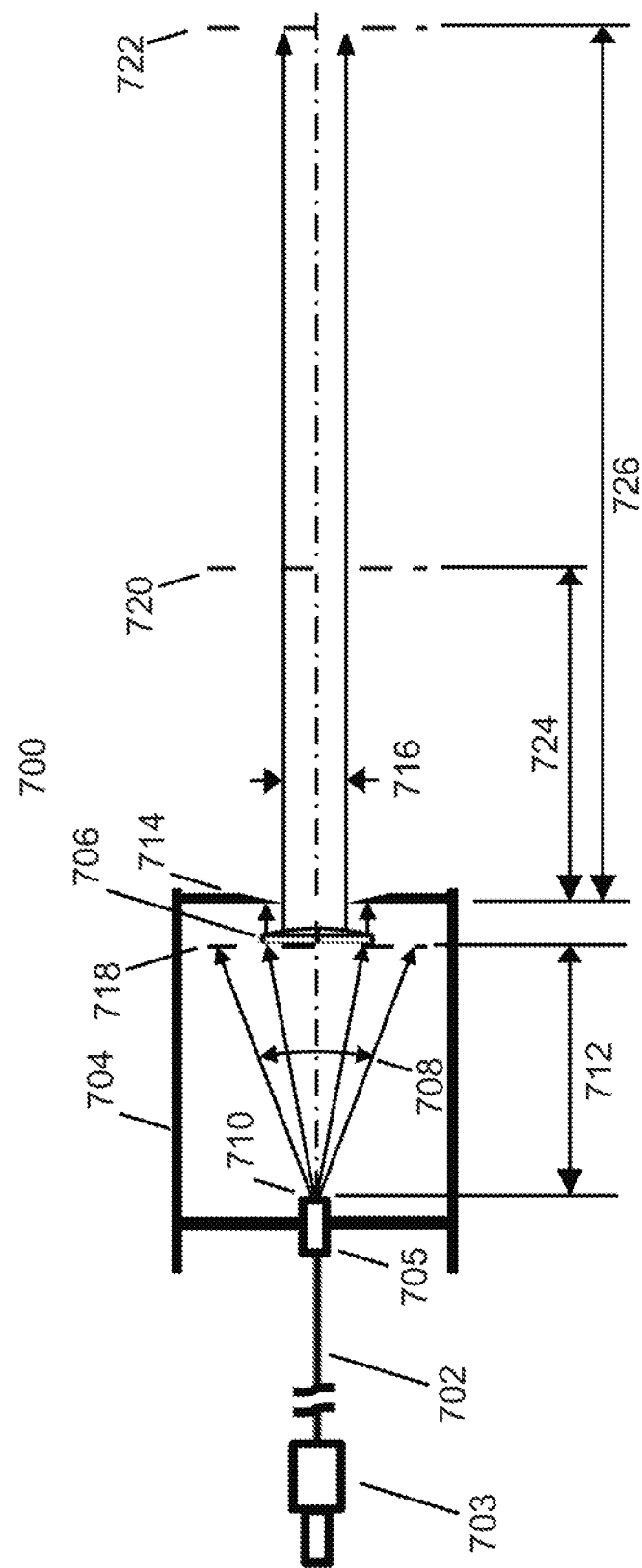
FIG. 42A is a graphical depiction of another exemplary embodiment of a frontal light diffusing device according to the present invention.
Figure 42B:
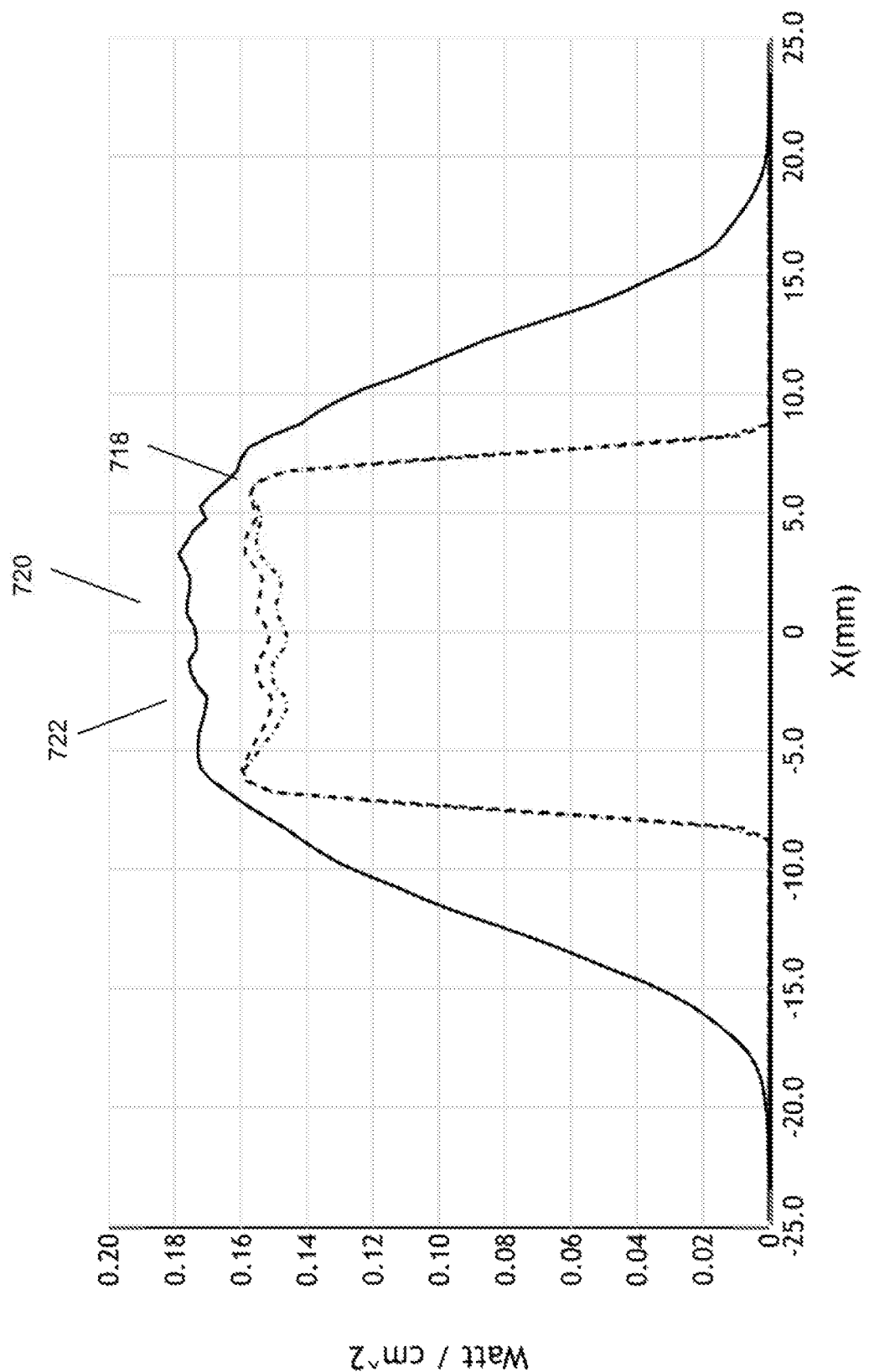
FIG. 42B is a graph of the spatial irradiance distributions along a vertical cross section (718) of the frontal light diffusing device of FIG. 42A and along vertical cross sections (720, 722) of the targeted treatment area at two standoff distances (724, 726) by the frontal light diffusing device in FIG. 42A.

Referring to FIG. 42A, the present invention provides a frontal light diffusing device 700 that satisfies these goals comprising an optical fiber 702 with a proximal connector 703, a distal termination 705, and a collimation lens assembly 704. The optical fiber 702 can be a cylindrical fiber, a non-circular core fiber (e.g., 302, 604), or a combination thereof discussed above. The collimation lens assembly 704 includes a collimation lens 706, which can be constructed of a transparent optical material, i.e. glass, crystal, a transparent polymer, or a reflective material. The collimation lens 706 can be comprised of a single optical element or a combination of optical elements. The collimation lens 706 can have any combination of spherical, aspherical, refractive, diffractive or reflective surfaces and the materials can have a graded index profile. The naturally divergent light output 708 of the fiber 702 is allowed to expand until it encounters the collimation lens 706. The fiber 702 is located so its output face 710 is approximately at the back focal length 712 of the collimation lens 706. A variable aperture 714 is located near or at the output of the collimation lens 704 where it can block portions of the light output 708, producing a light output beam 716 with extent that corresponds to the opening in 714. As shown in FIG. 42A, only the central portion of the light output 708 from the fiber 702 is allowed through the aperture 714 (i.e., collimated light output 716). This resulting collimated light output 716 has a "top hat" irradiance distribution as shown in FIG. 42B that is essentially the same magnitude (e.g., less +/−20% difference in values, less than +/−15% difference in values, or even +/−10% difference in values) in (i) the near field (e.g. cross section 720 at a standoff distance of 724), (ii) the far field (e.g. cross section 722 at a standoff distance of 726), and the distance in between the near field and the far field, hereinafter defined as "flat irradiance distribution".

The expanding cone of rays out of the fiber 702 is deliberately allowed to overfill the collimating lens 706. The solid line in the plot in FIG. 42B is the irradiance distribution measured at location 718 shown in FIG. 42A. The portions of the distribution with high variation are allowed to land on the structure of the collimation lens 704 and are blocked, reflected or absorbed. Only the uniform central portion of the irradiance distribution passes through both the collimation lens 706 and the variable aperture 714 to generate output beam 716, resulting in the flat irradiance distribution 720, shown as a dashed line in FIG. 42B.

The aperture 714, located on the output side of the collimation lens 704 blocks portions of the light output 708 that are not desired. In a preferred embodiment, the aperture 714 is an iris that allows the beam size to be varied from 1 mm to 12 mm in diameter. Alternatively, the aperture 714 could be configured to produce a square, rectangular, or even a non-symmetric light output.

The collimated light output 716 after the aperture 714 has very low divergence, so that the light output 718 is approximately the same size in the near field, at location 720 in FIG. 42A as it is in the far field, at location 722 in FIG. 42A. Referring to FIG. 42B, this resulting flat irradiance distributions at cross section 720 (shown as a dashed line) and cross section 722 (shown as a dash-dot line) have very close to flat top irradiance distribution and the beam size does not change significantly with distance (hereinafter defined as "flat irradiance distribution").

In one exemplary embodiment of the frontal light diffusing device 700, the input fiber has a core diameter of 400 um and a clad diameter of 430 um and is filled with 1.01 Watts of 690 nm light having a numerical aperture of 0.29. The collimation lens 706 is comprised of a plano-convex lens with a 25 mm diameter and a focal length of 75 mm. In this embodiment, the amount of excess optical power absorbed by the hand piece when generating a 12 mm diameter beam of 150 mWatt/cm$^2$ at 720 is less than 0.85 Watts, which is easily dissipated by the body of the hand piece. Referring to FIGS. 41A-42B, the flat irradiance distribution at cross section 720 is measured at the standoff distance 724 of 100 mm from the aperture 714 and the flat irradiance distribution at cross section 722 is measured at the standoff distance 726 of 200 mm from the aperture 714.

The performance of this embodiment 700 presents several advantageous characteristics. First, the size and geometry of the light output can be adjusted over a wide range without variation to the irradiance (mWatt/cm$^2$) at the target. Secondly, the irradiance created on the target has very little dependence on the standoff distance between the projector and the target. These features make it easy to calibrate the output of the light source to generate the desired levels of treatment light and make it easier for the operator to position the illuminator to achieve the desired exposure levels. Please note that the light output of an unmodified cylindrical optical fiber 702 was used in FIG. 42A. If an angular mode mixing section or a non-circular core fiber section (e.g., 302, 606) was used that created a more uniform, flat top angular distribution than 718 in FIG. 42B, then a wider output beam could be obtained. Additionally, a non-circular core input fiber could be used.

Example I

Figure 6:
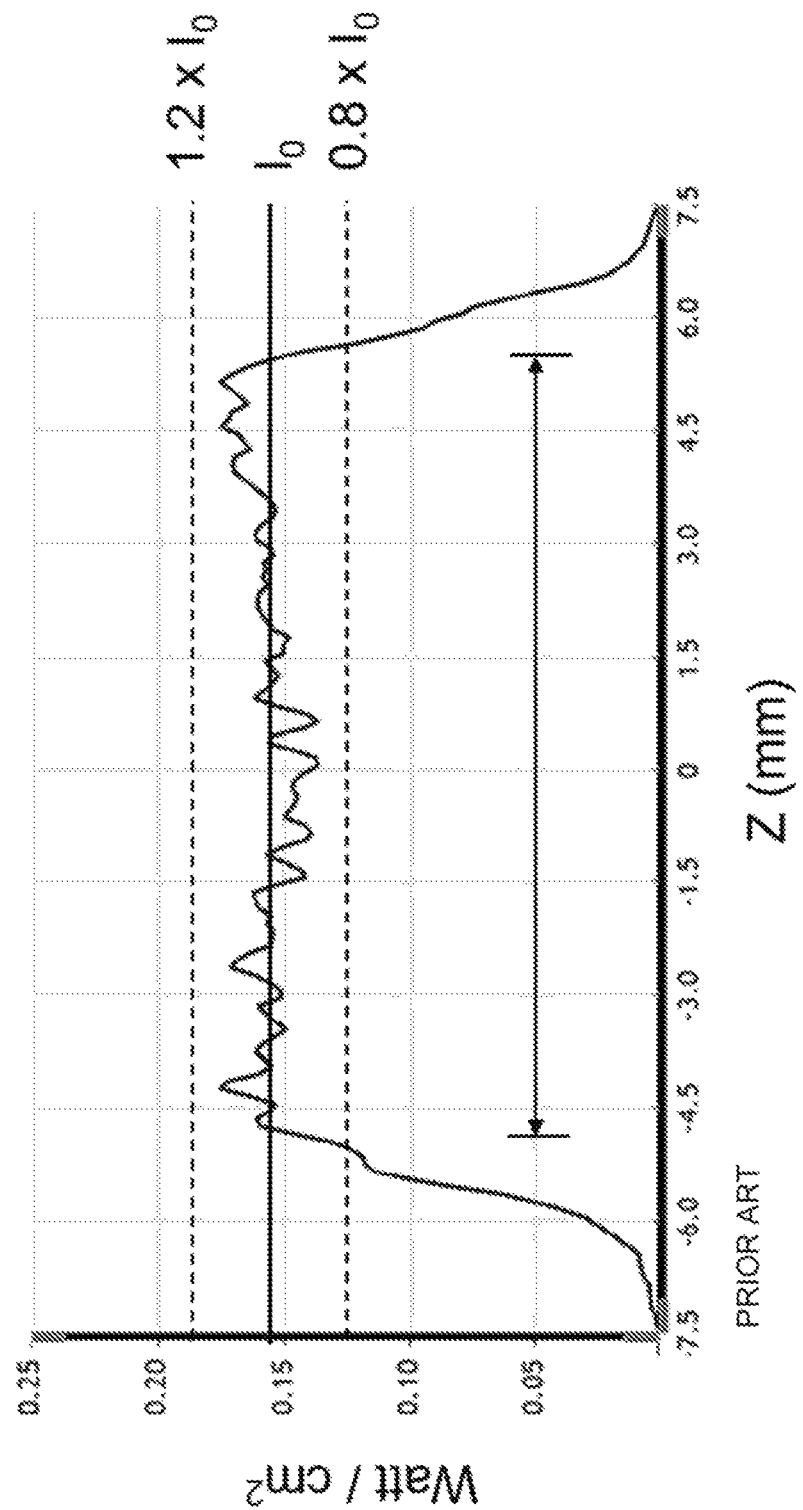
FIG. 6 is a graph of the out-coupled longitudinally radially-symmetric irradiance distribution of the cylindrical light diffusing device of FIG. 3.
Figure 7:
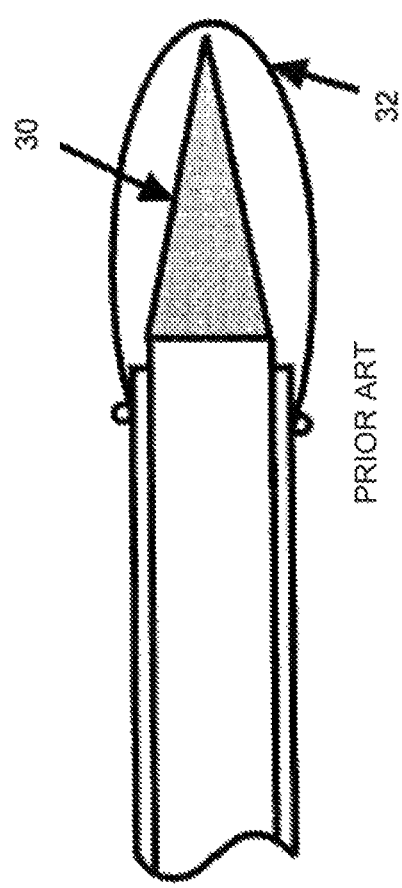
FIG. 7 is a graphical depiction of a prior art exemplary cylindrical light diffuser.
Figure 8:
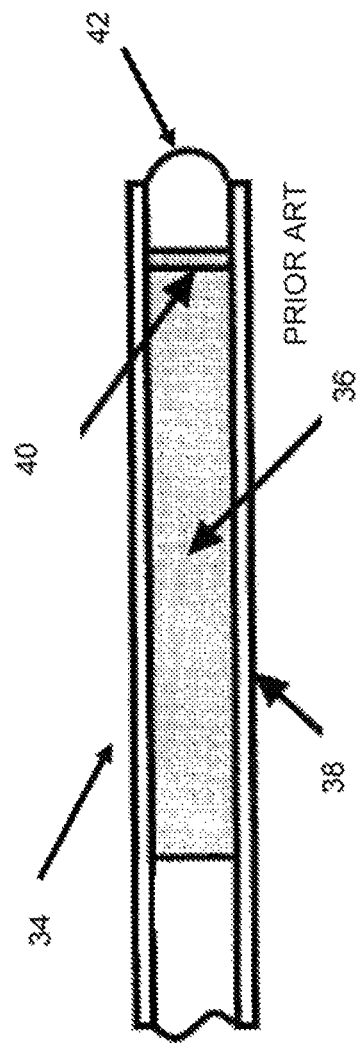
FIG. 8 is a graphical depiction of another prior art exemplary cylindrical light diffuser.
Figure 28:
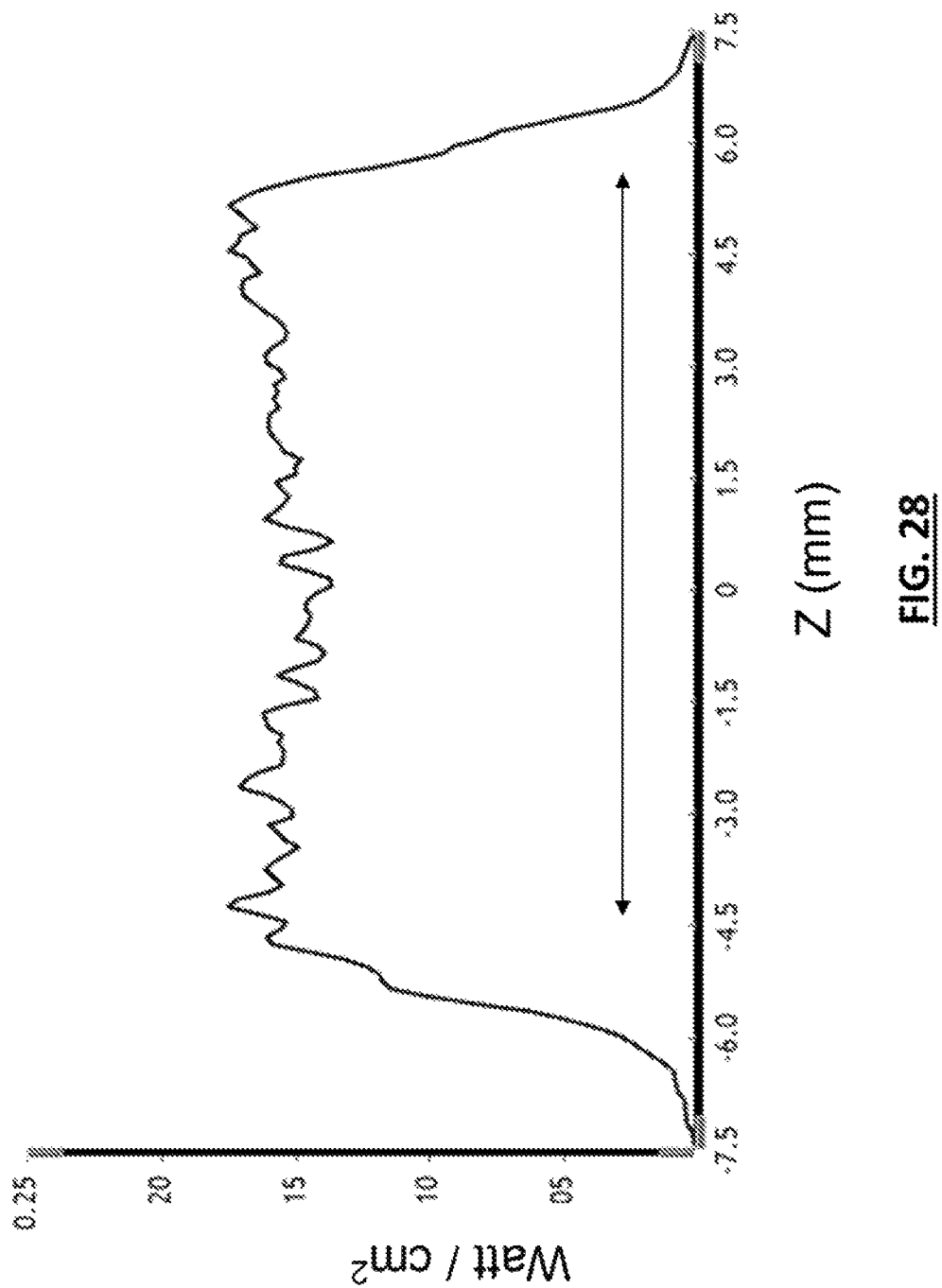
FIG. 28 is a graph of the out-coupled longitudinally radially-symmetric irradiance distribution of the cylindrical light diffusing device of FIGS. 9, 10, and 14.
Figure 32:
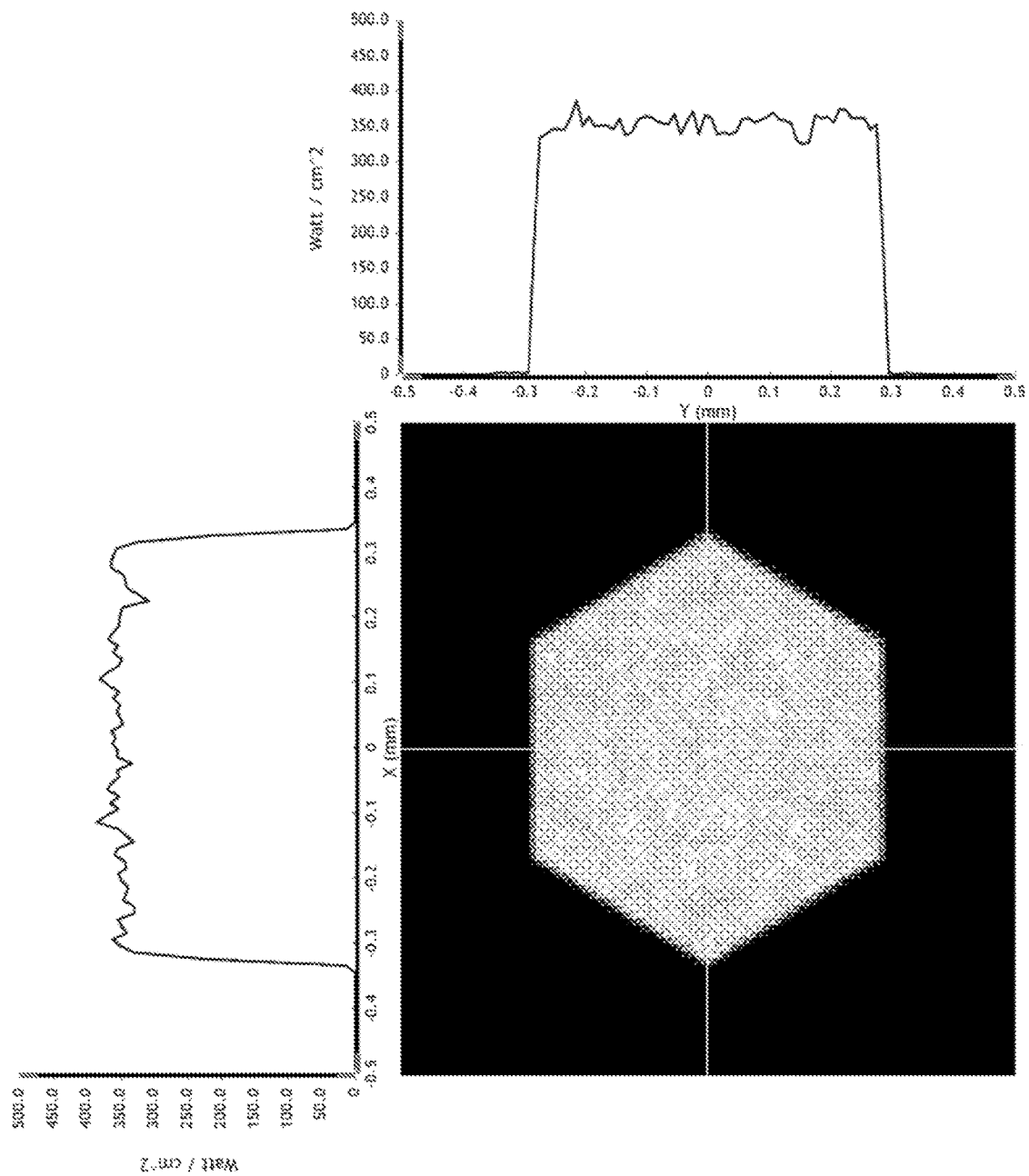
FIG. 32 is a map of the irradiance at a vertical cross-section of the optical fiber of the cylindrical light diffusing device of FIG. 31 and its associated irradiance distribution graphs.
Figure 35:
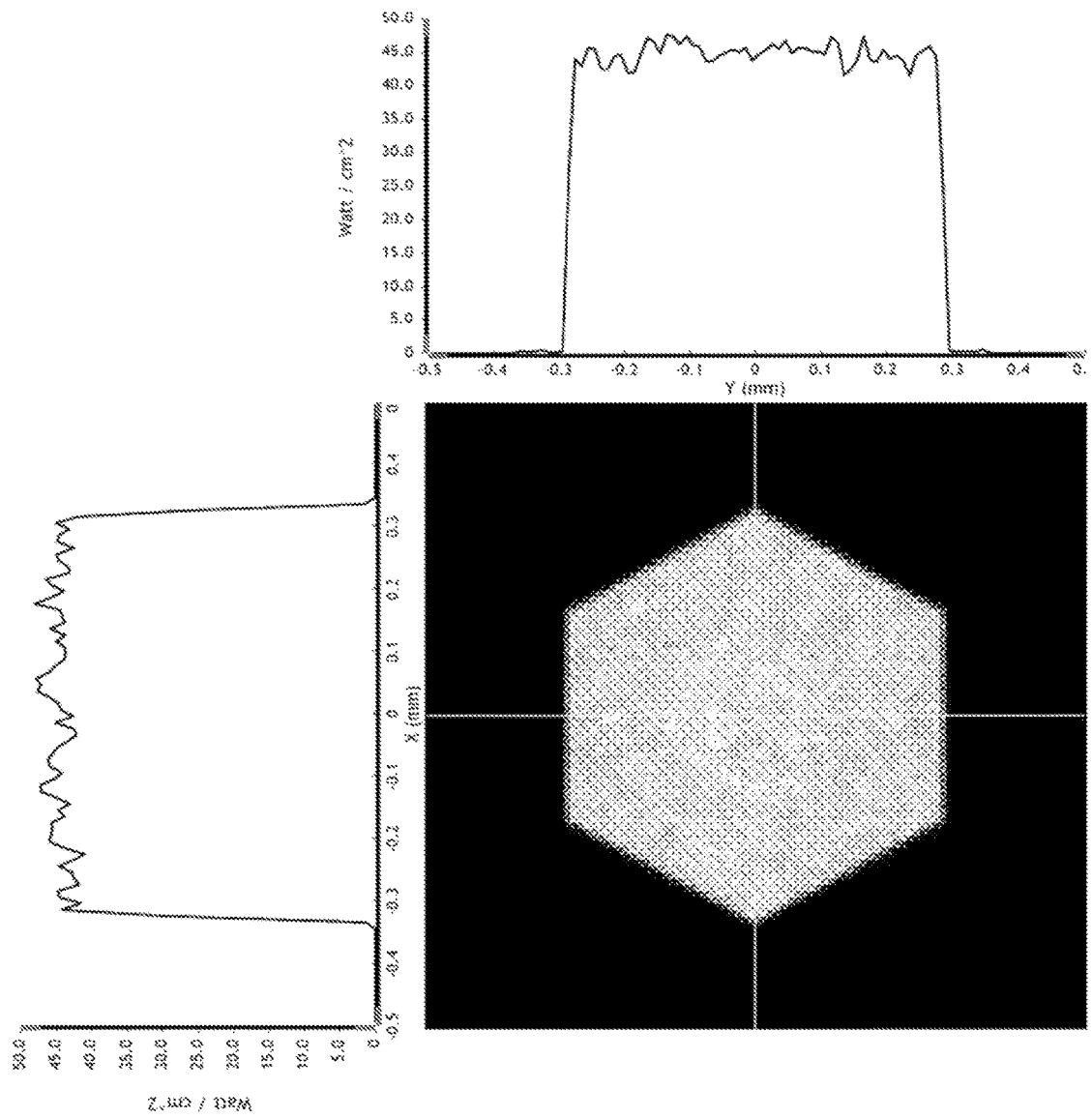
FIG. 35 is a map of the irradiance at a vertical cross-section of the optical fiber of the cylindrical light diffusing device of FIGS. 11 and 12 and its associated irradiance distribution graphs.
Figure 36:
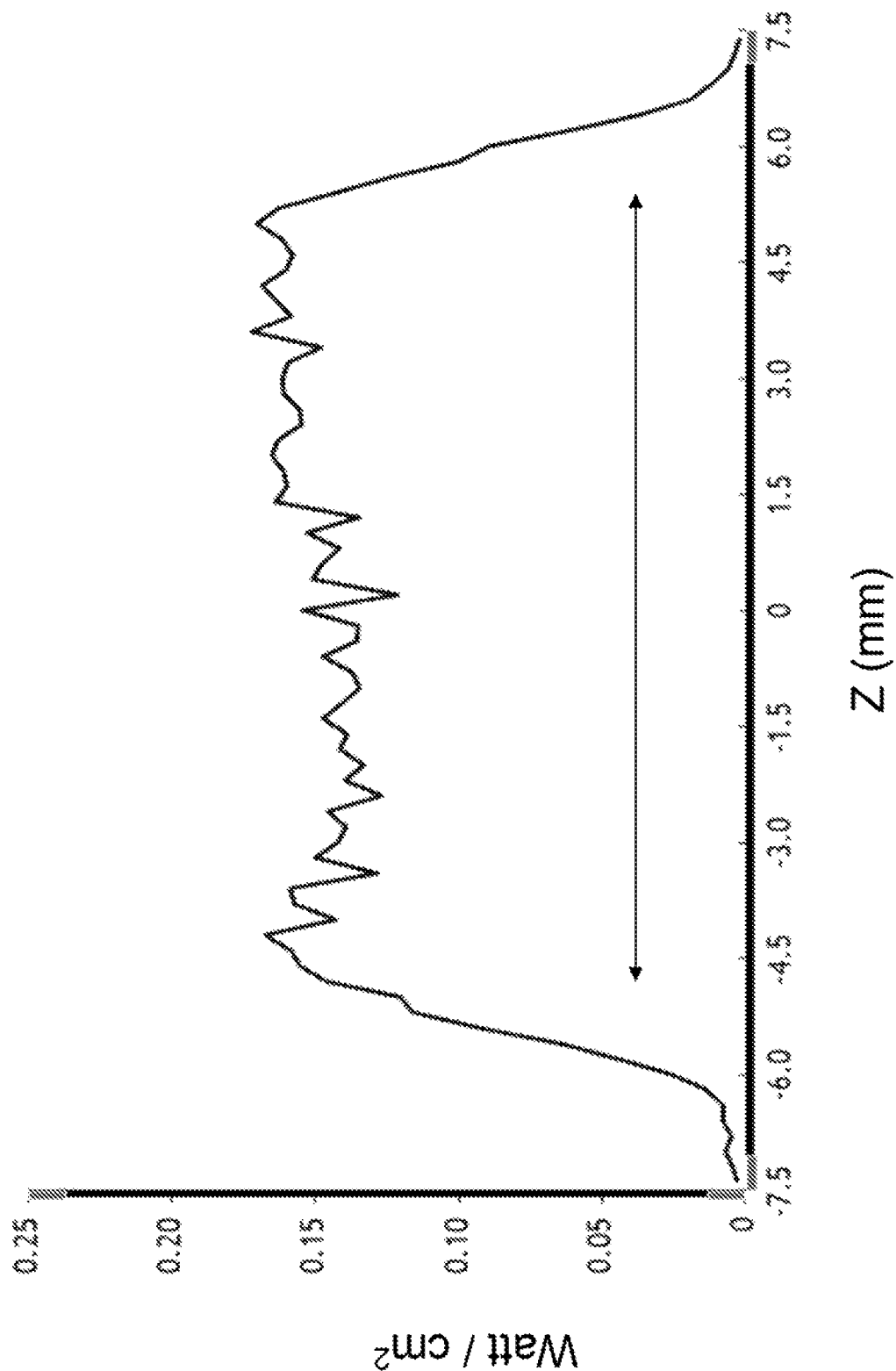
FIG. 36 is a graph of the out-coupled longitudinally radially-symmetric irradiance distribution of the cylindrical light diffusing device of FIGS. 11 and 12.
Figure 37A:
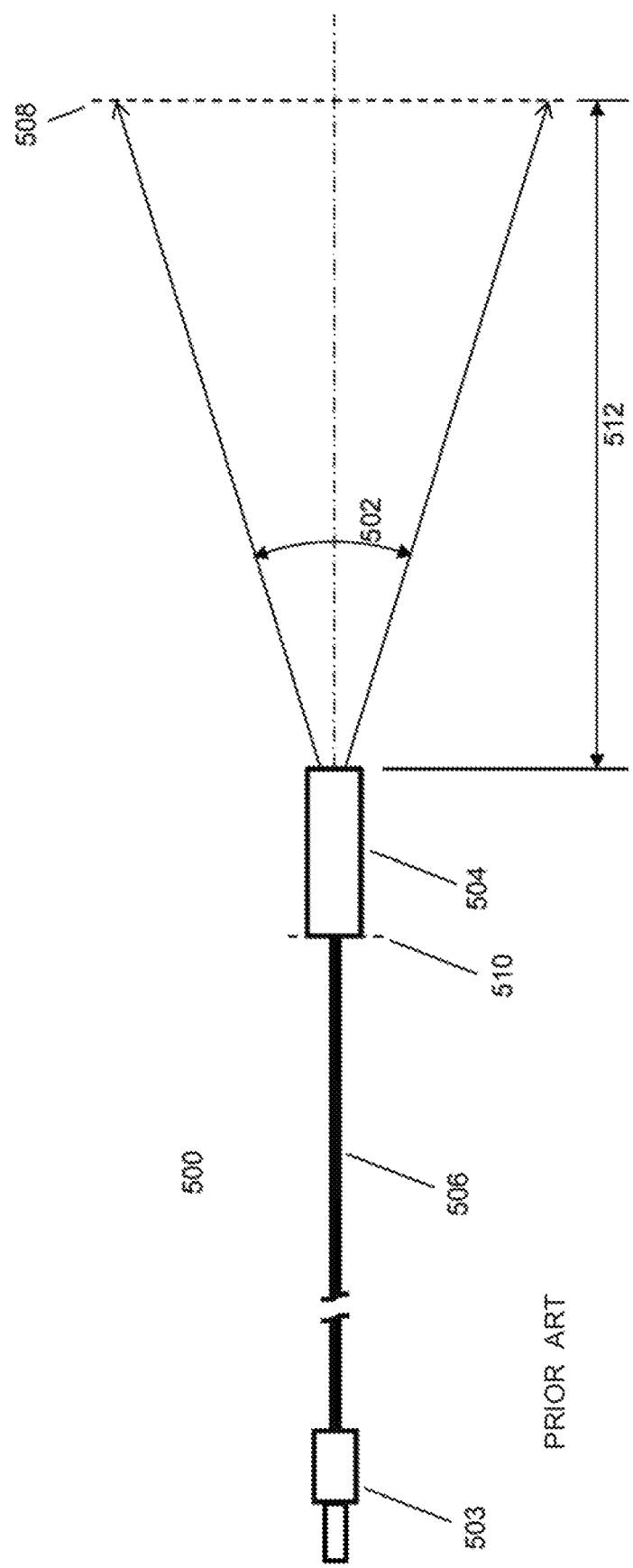
FIG. 37A is a graphical depiction of a prior art exemplary frontal light diffusing device.
Figure 37B:
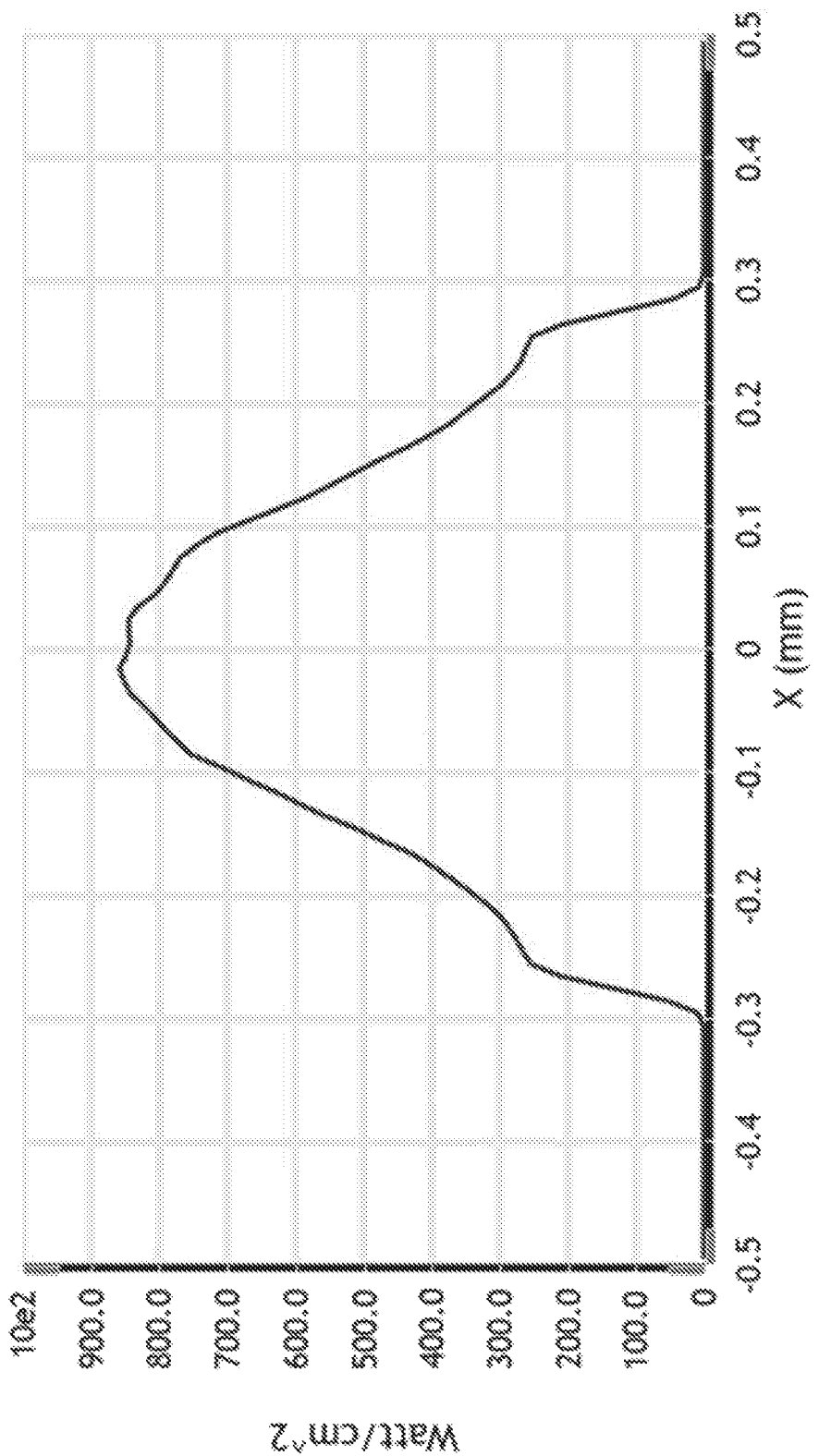
FIG. 37B is a graph of the spatial irradiance distribution along a vertical cross section (510) of the optical fiber of the frontal light diffusing device in FIG. 37A.
Figure 37C:
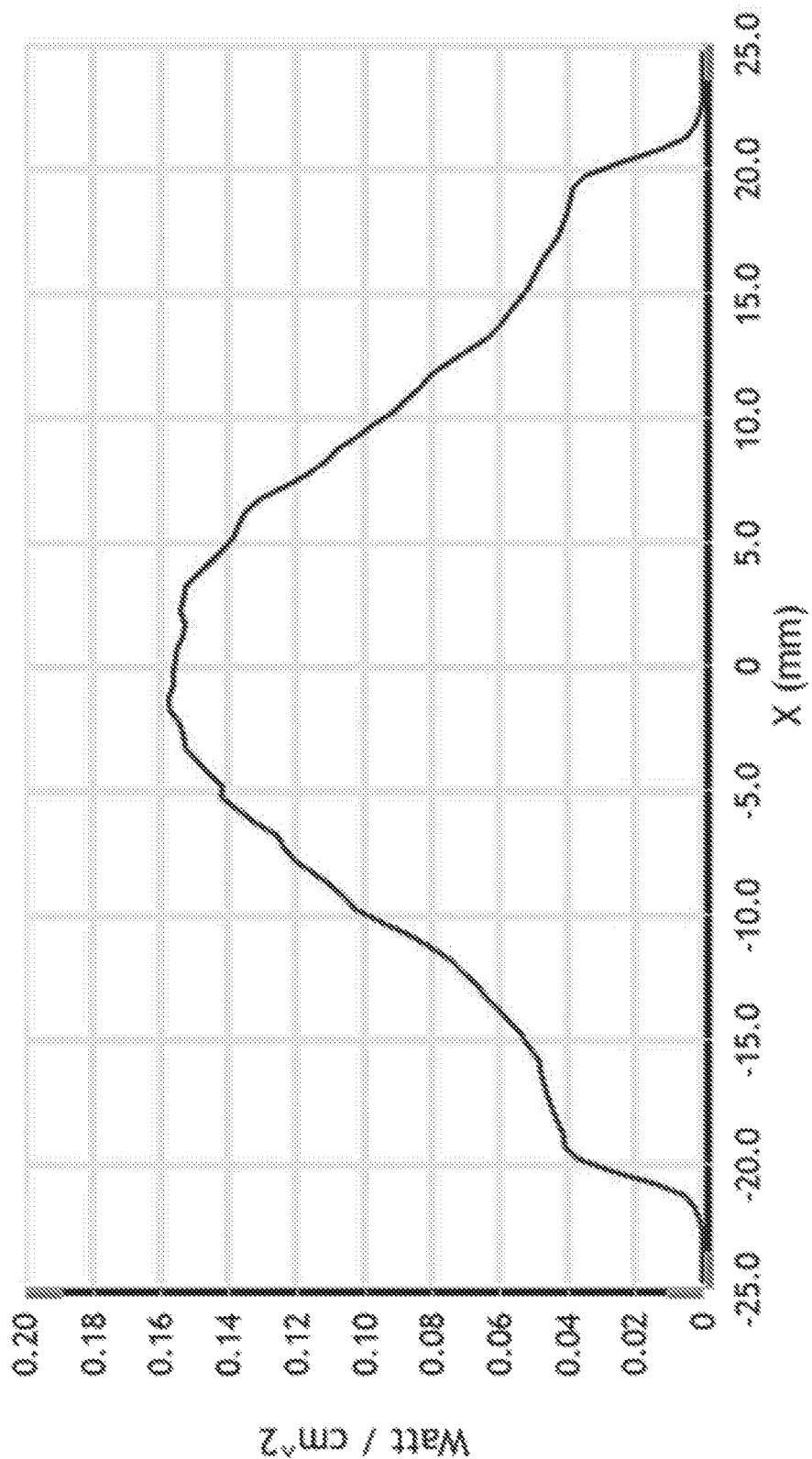
FIG. 37C is a graph of the spatial irradiance distribution along a vertical cross section (508) of the target by the frontal light diffusing device in FIG. 37A.
Figure 38A:
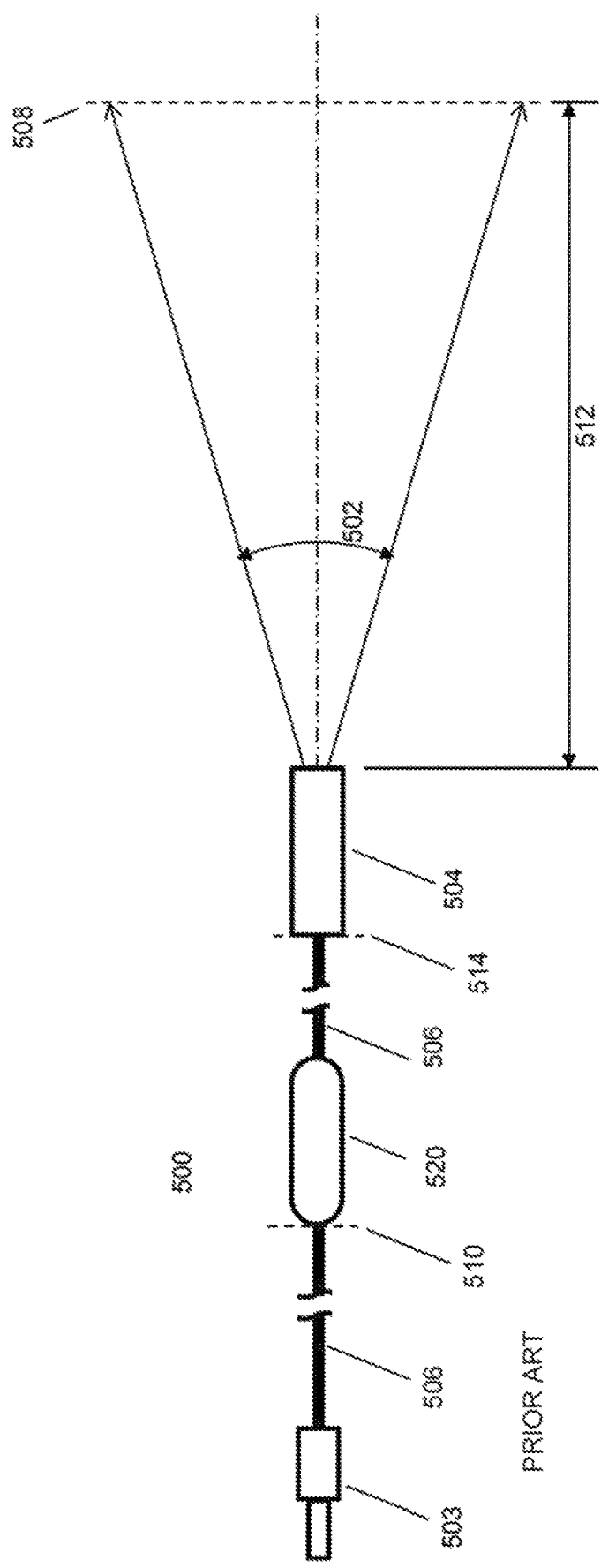
FIG. 38A is a graphical depiction of a prior art exemplary frontal light diffusing device with a mode mixing section.
Figure 38B:
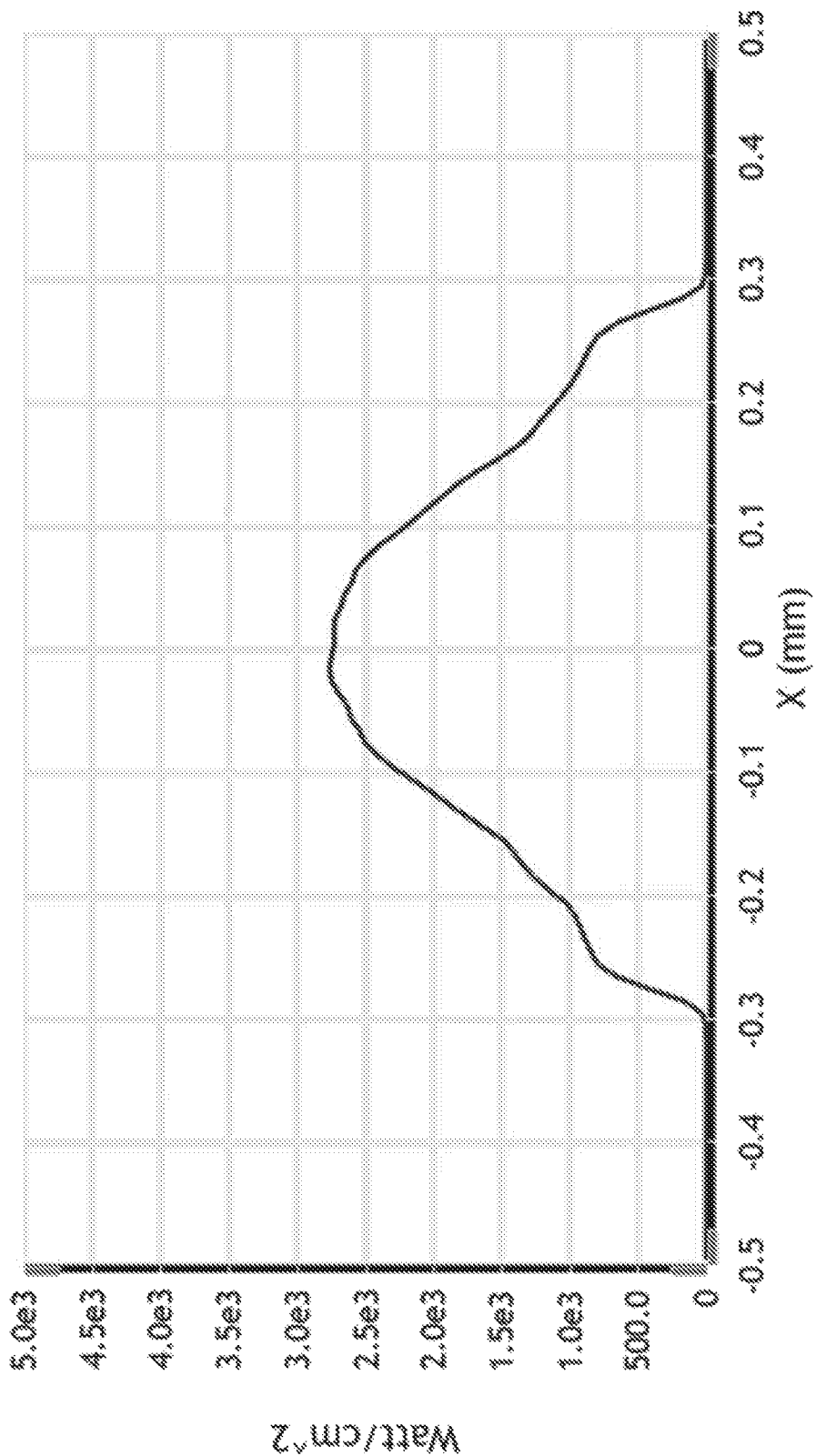
FIG. 38B is a graph of the spatial irradiance distribution along a vertical cross section (510) of the optical fiber of the frontal light diffusing device in FIG. 38A.
Figure 38C:
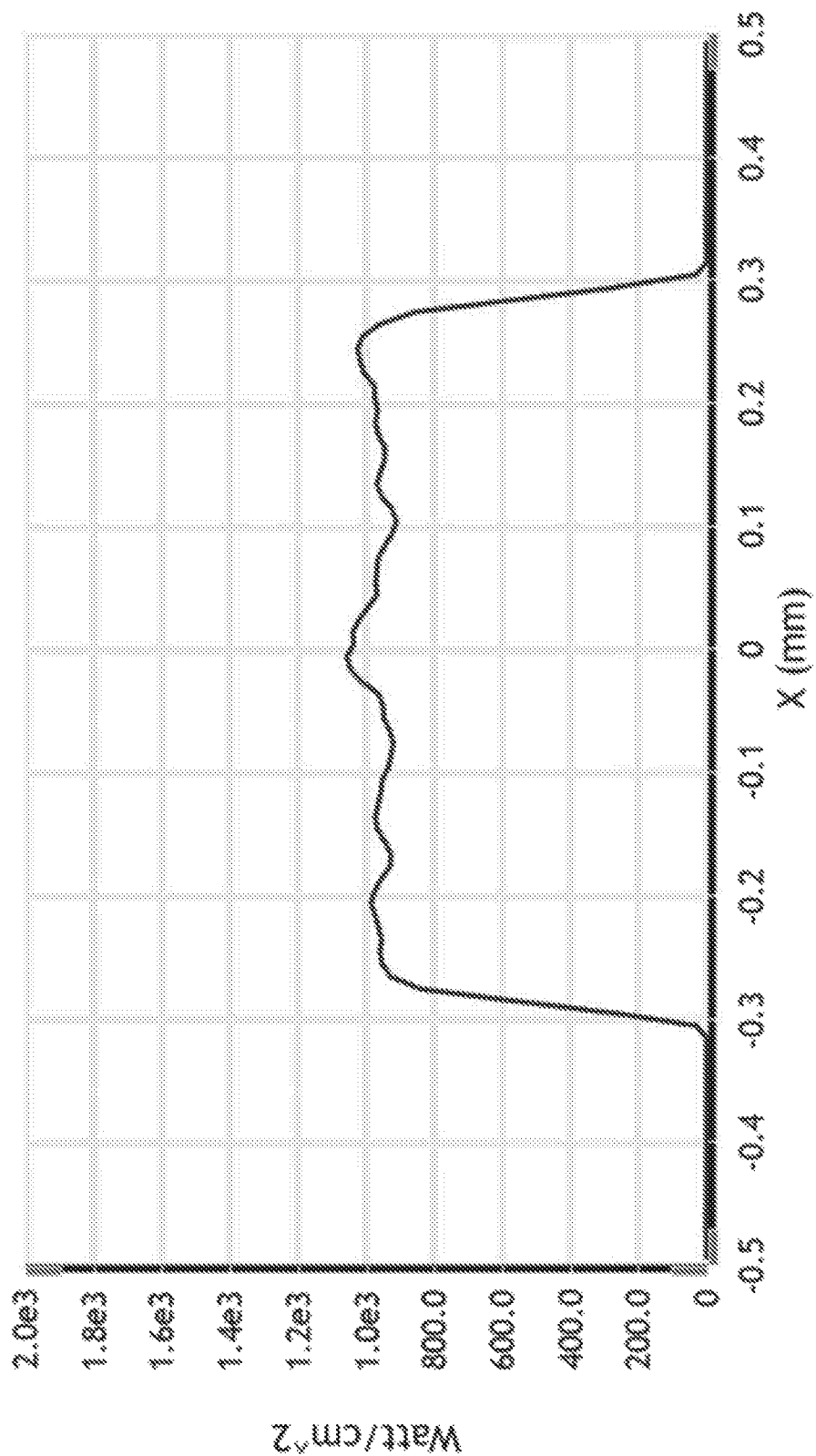
FIG. 38C is a graph of the spatial irradiance distribution along a vertical cross section (514) of the optical fiber of the frontal light diffusing device in FIG. 38A.
Figure 38D:
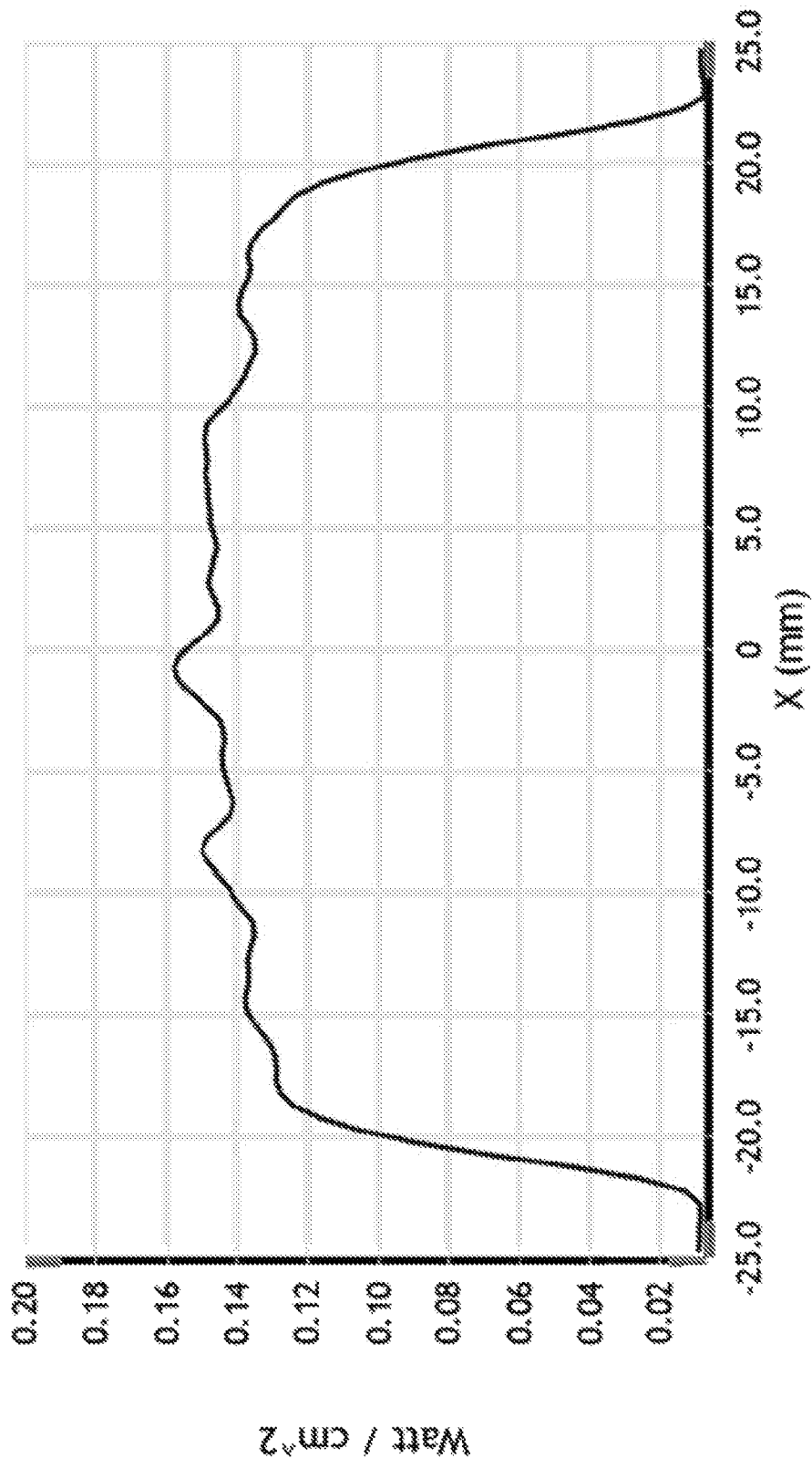
FIG. 38D is a graph of the spatial irradiance distribution along a vertical cross section (508) of the target by the frontal light diffusing device in FIG. 38A.
Figure 39A:
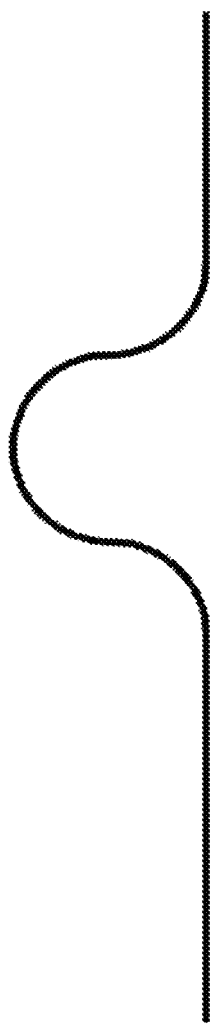
FIG. 39A is a graphical depiction of a prior art fiber optic mode mixing section with four quarter turns with small radii.
Figure 39B:
FIG. 39B is a graphical depiction of a prior art fiber optic mode mixing section with twelve quarter turns with small radii.
Figure 39C:
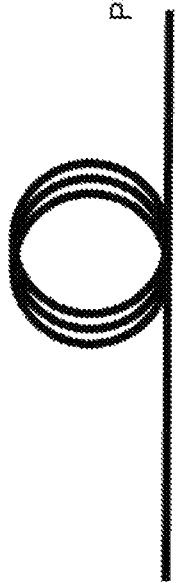
FIG. 39C is a graphical depiction of a prior art fiber optic mode mixing section with three small radius loops formed around an axis perpendicular to the axis of the fiber.
Figure 39D:
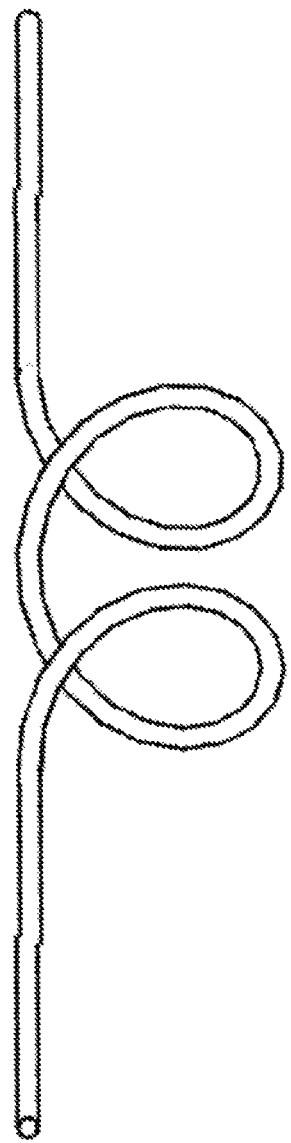
FIG. 39D is a graphical depiction of a prior art fiber optic mode mixing section with two helical loops formed around an axis parallel to the axis of the fiber.

In one embodiment and referring to FIG. 31, a cylindrical light diffusing device 400 is provided wherein it (400) is exactly the same as the cylindrical light diffusing device 100 discussed above except that it (400) has the non-circular core fiber 302 instead of the conventional circular optical fiber 12 of the device 100. The vertical (i.e., latitudinal) cross-sectional view of the non-circular core fiber 302 is the same as the embodiment shown on FIG. 14. Using a 690 nm laser with 1 Watt launch power as the light source and adjusting the power until the irradiance measured at the center 17 of the longitudinal length of the diffuser 16 was 150 mW/cm$^2$ resulted in the "top hat" core irradiance distribution shown in FIG. 32. The irradiance measurement value of 150 mW/cm$^2$ is measured 0.75 mm from the central axis of the stated location of the diffuser 16. FIG. 32 shows the core irradiance distribution at the vertical cross-section (e.g., shown as "11" in FIG. 31) through the non-circular core fiber 302 taken just before the cylindrical diffuser 16. The associated irradiance distribution graphs shown in FIG. 32 taken from vertical and horizontal cross sections through the center of the map of the irradiance show the same "top hat" core irradiance distribution as the above-discussed conventional cylindrical light diffusing device 200, which requires a mode mixer (24). This "top hat" core irradiance distribution indicates a high degree of uniformity of the irradiance distribution in the fiber core 350. This demonstrates that including a non-circular core fiber 302 prior to a cylindrical diffuser 16 can improve the irradiance or light output characteristic of the device 400. However, please note that the device 400 cannot achieve the "top hat" diffusing irradiance distribution as shown in FIGS. 6, 28 and 35 unless the construction of the cylindrical diffuser 16 is optimized to account for the launch conditions. The present invention includes the device 400 with such optimized cylindrical diffuser 16 in order to deliver the "top hat" diffusing irradiance distribution as shown in FIGS. 6, 28 and 36

Example II

Figure 1:
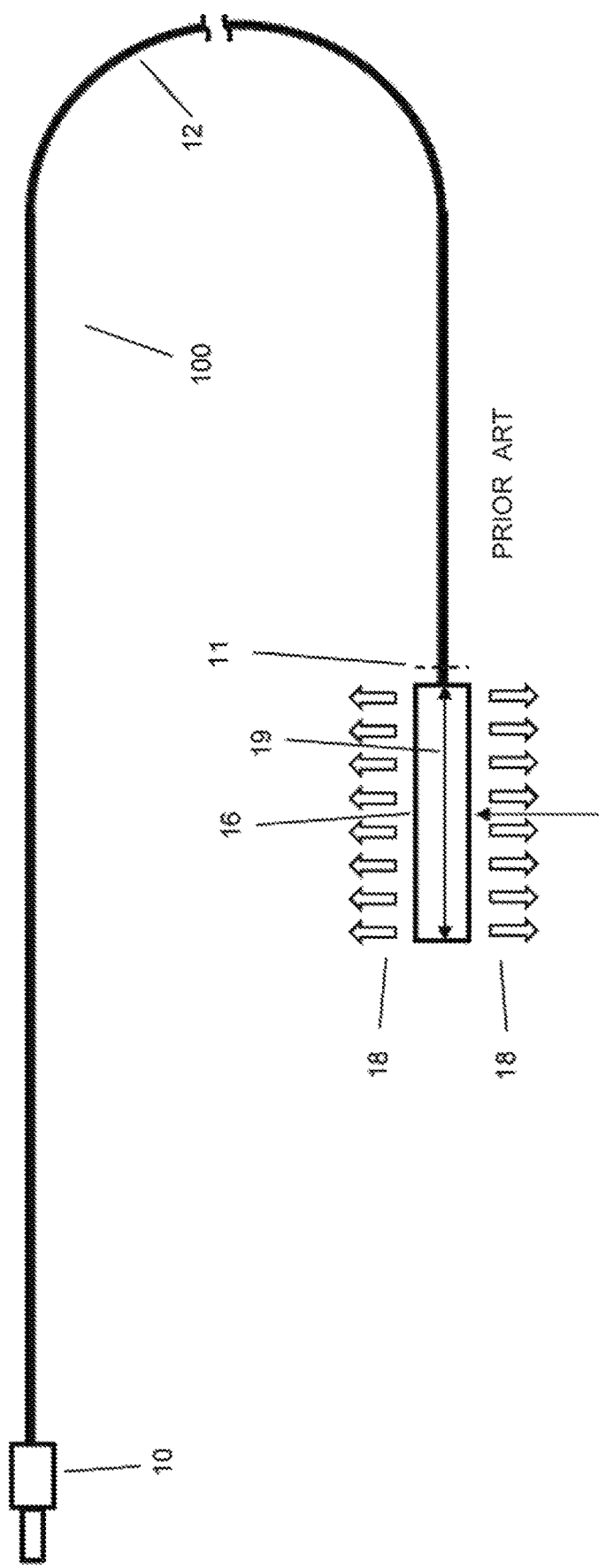
FIG. 1 is a graphical depiction of a prior art exemplary cylindrical light diffusing device.
Figure 2:
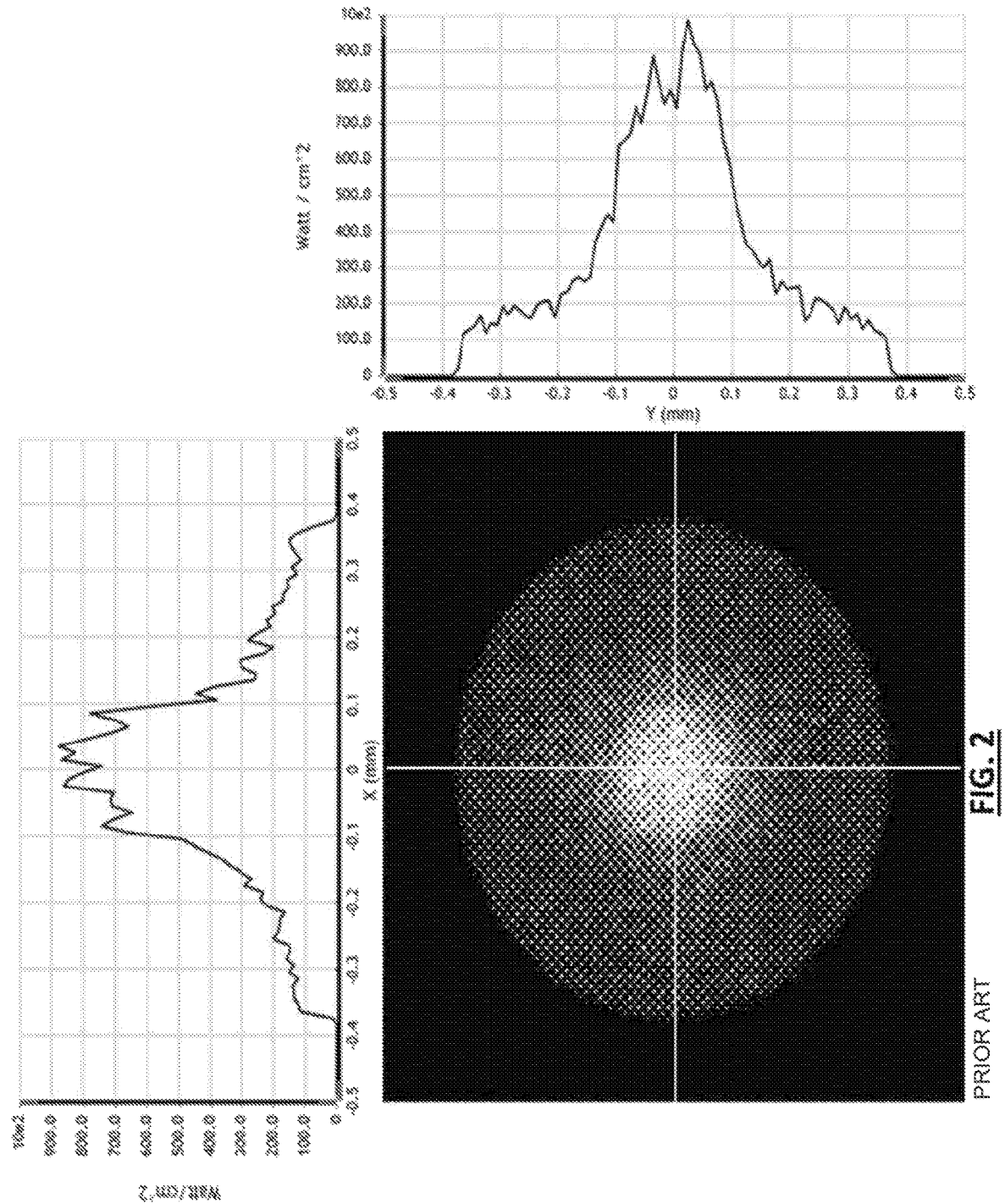
FIG. 2 is a map of the irradiance at a vertical cross-section of the optical fiber of the cylindrical light diffusing device of FIG. 1 and its associated irradiance distribution graphs.
Figure 3:
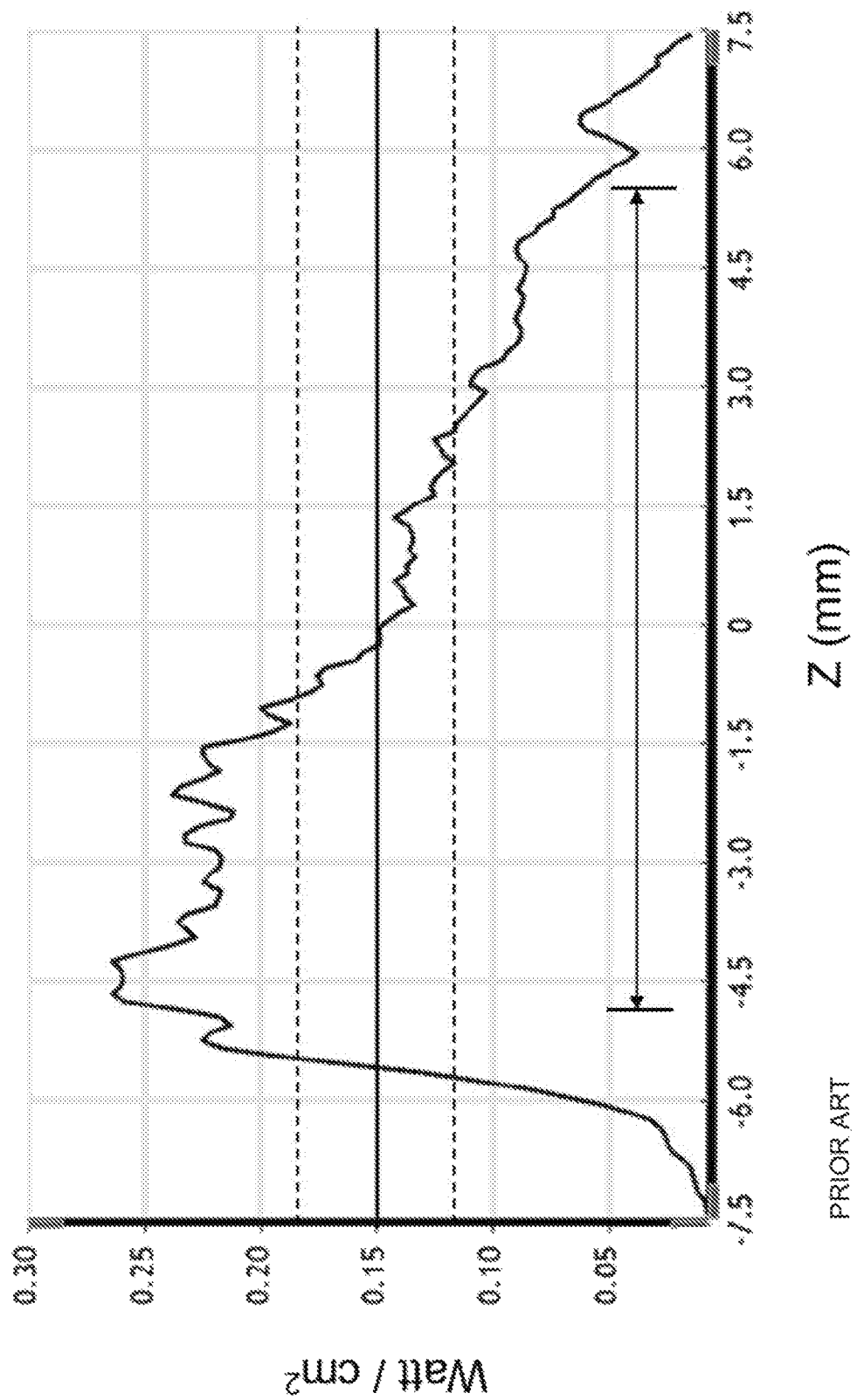
FIG. 3 is a graph of the out-coupled longitudinally radially-symmetric irradiance distribution of the cylindrical light diffusing device of FIG. 1.
Figure 33:
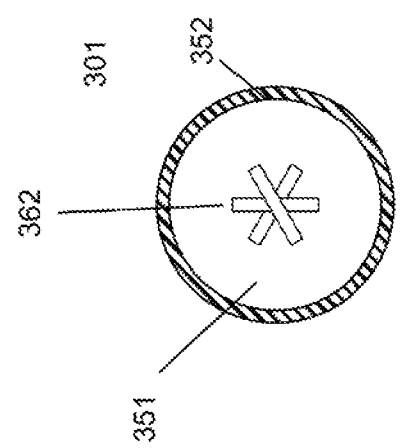
FIG. 33 is a vertical cross-section view of a circular shaped core fiber exemplary embodiment at a location with internal scattering features.
Figure 34:
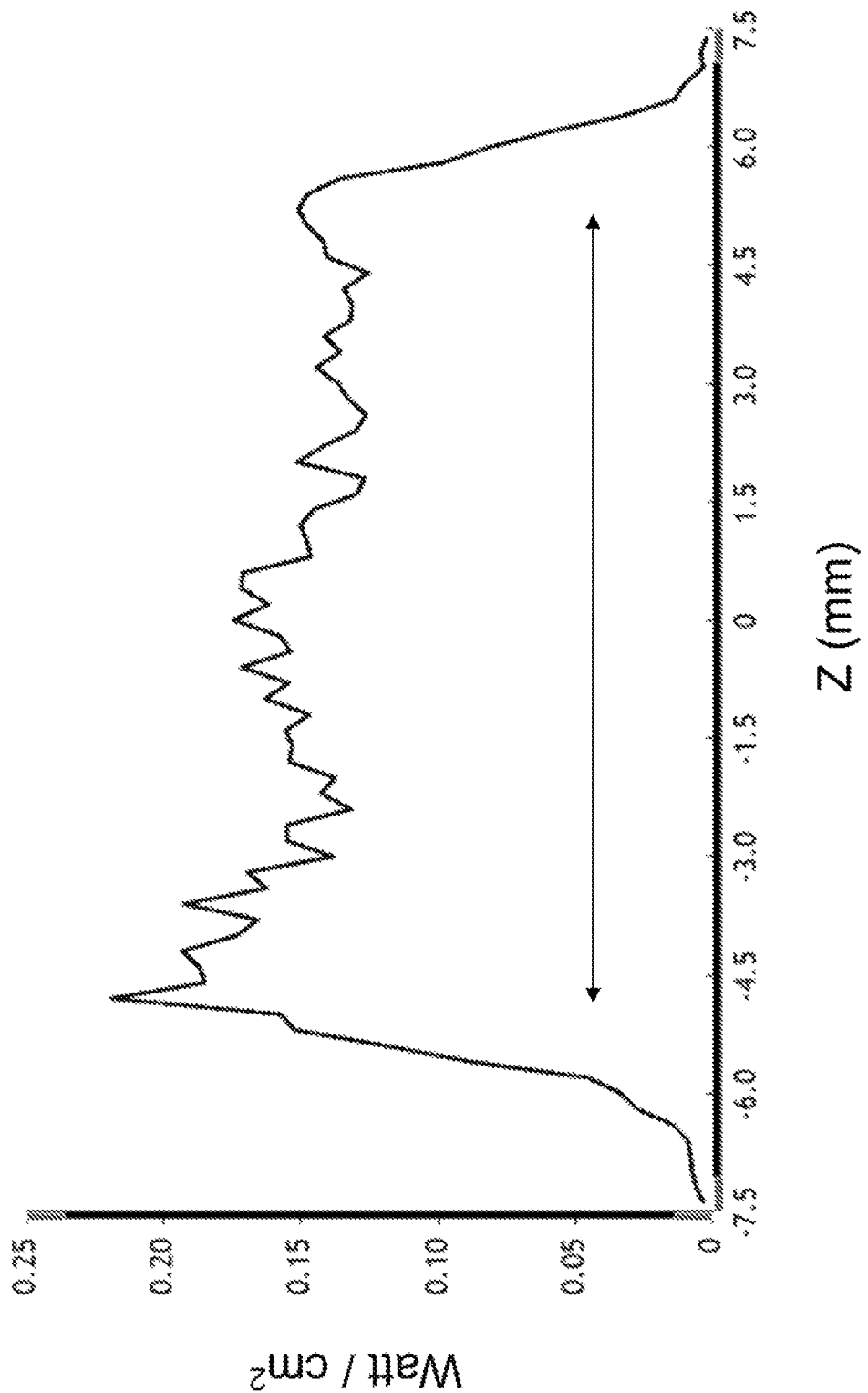
FIG. 34 is a graph of the out-coupled longitudinally radially-symmetric irradiance distribution of the cylindrical light diffusing device of EXAMPLE II.

In another embodiment of the present invention, a cylindrical light diffusing device is provided. This device has the same components as the device 400 discussed above in EXAMPLE I and shown in FIG. 31 except that the cylindrical diffuser 16 is now a conventional circular core optical fiber having a light emitting section containing internal scattering features 362 as shown in FIG. 33. FIG. 33 shows a vertical cross sectional view of this circular core fiber's 301 light emitting section having its cladding 352 and its circular fiber core 351, which contains internal scattering features 362. Using a 690 nm laser with 0.2 Watt launch power as the light source and adjusting the power until the irradiance measured at the center 17 of the longitudinal length of the circular core fiber's light diffusing section was 150 mW/cm², this device resulted in the diffusing irradiance distribution shown in FIG. 34 which provides a generally "top hat" diffusing irradiance distribution. The irradiance measurement of 150 mW/cm² is measured 0.75 mm from the central axis of the stated location of the light diffusing section. The diffusing irradiance distribution shown in FIG. 34 is closer to the optimal "top hat" diffusing irradiance distribution shown in FIGS. 6, 28, and 36 especially when compared to the diffusing irradiance distribution of the device 100 shown in FIG. 3. For the purpose of this specification, the term "top hat" diffusing irradiance distribution shall include both the generally "top hat" diffusing irradiance distribution shown in FIG. 34 and the optimal "top hat" diffusing irradiance distribution shown in FIGS. 6, 28, and 36.

FIG. 34 shows that there is a potential for sub-optimal efficiency and efficacy when using internal scattering features 362 in a circular core optical fiber to create a light diffusing section intended to emit the desired "top hat" diffusing irradiance distribution because as the light propagates forward in the light emitting section, the irradiance in the optical axis of the optical fiber will gradually be depleted as the light encounters subsequent scattering features and leaves the light diffusing section. Since there is no mode mixing within this circular core light diffusing section, the vertical cross-sectional irradiance pattern will be less uniform, with the irradiance higher near the edges of the fiber core and depleted near the center where the scattering features are located.

This demonstrates that it is more desirable to use a non-circular fiber core 350 than a circular fiber core for the light emission section containing the internal scattering features 362. Nevertheless, the present invention includes the cylindrical light diffusing device presented in this example and its generally "top hat" diffusing irradiance distribution because it is possible this device and its generally "top hat" diffusing irradiance distribution are sufficient for certain applications.

Example III

In one exemplary embodiment of the device 300 and referring to FIGS. 9, 10, and 14, the device 300 includes the non-circular core fiber 302, the lead-in optical fiber 304, the at least one optical connector 306. During operation, the lead-in optical fiber 304 is in light communication to (i) a light source (not shown) and (ii) the non-circular core fiber 302 via the at least one optical connector 306. The lead-in fiber 304 has a 200 μm OD glass core and a 230 μm OD cladding. The length of the non-circular core fiber 302 is 30 cm, which distally terminates into the light blocking means 314 made out of a reflecting coating of aluminum deposition. During operation, the non-circular core fiber 302 is filled with laser light having an angular distribution of a NA of 0.22.

Referring FIGS. 10 and 14, the fiber core 350 of the non-circular core fiber 302 is constructed out of PMMA with a hexagonal geometry in a circumscribed ø660 μm diameter circle. The fiber core 350 is cladded by the cladding 352 with an interior surface geometry 356 that has the same hexagonal geometry as the fiber core 350. However, the exterior surface geometry 354 of the cladding 352 is circular. The cladding 352 is constructed of a silicone with a ø740 μm OD.

The non-circular core fiber 302 further includes the light diffusing section 308 having the diffusing proximal end 310 and the diffusing distal end 312. The light diffusing section 308 is 10.8 mm in longitudinal length and the internal scattering features 362 begin at the diffusing proximal end 310 and ends at the diffusing distal end 312. The features 362 are comprised of 27 sets of three cylinders. Each cylinder is approximately 27 μm in diameter and 270 μm in length oriented around the central axis 364 at 60° increments as shown in FIGS. 9 and 10. The 27 sets of the features 362 are arranged based upon the following formula in a non-linear fashion: $z_i = 0.5i + 0.0045i^2 - 0.0003i^3$ where the index i is an integer with values from 0 to 26 and $z_i$ is the relative z location of the $i^{th}$ feature 362 along the axis 364. Please note that the present invention is not limited to this formula, the size of the features 362, the number of features 362 per unit length of the diffusing section 308, or the amount of scattering per feature 362. Instead, the present invention includes other suitable spacing's, sizes, numbers of features 362 per unit length, and amounts of scattering per feature 362.

Furthermore, the following characteristics of the device 300 may be adjusted in order to further optimize its diffusing irradiance distribution: the longitudinal length and diameter of the diffusing section 308, the size and geometry of the fiber core 350 and any cladding 352, the scattering characteristics of the features 362, the maximum angle coming out the of the light source and/or the lead-in fiber 304, and the inclusion of the light blocking means 314 at the distal end of the non-circular core fiber 302. This optimization can be performed experimentally or using a ray tracing CAD program. The common factor in determining an optimal diffusing irradiance distribution is to engineer a linear increase in the effective scattering per incremental volume, as there is a linear decrease in the light density per incremental volume in the fiber core 350.

As discussed above, FIG. 27 shows a map of the irradiance at the vertical cross-section (shown as "316" in FIG. 9) through the fiber core 350 taken just before the diffusing proximal end 310 for this exemplary embodiment of the device 300. The light source used is a 690 nm laser with 0.125 Watt launch power and this power was adjusted until the irradiance measured at the center 307 of the longitudinal length of the light diffusing section 308 was 150 mW/cm². This measurement is taken 0.75 mm from the central axis of the stated location of the light diffusing section 308. The total length of optical fiber (combination of the lead-in fiber 304 and the non-circular core fiber 302) from the light source leading up to this location 316 is 2 meters long.

During operation, the non-circular core fiber 302 is filled with laser light having an angular distribution of a NA of 0.22.

The associated irradiance distribution graphs shown in FIG. 27 taken from vertical and horizontal cross sections through the center of the map of the irradiance show the same "top hat" core irradiance distribution as the above-discussed conventional cylindrical light diffusing device 200 containing a mode mixer 24. This "top hat" core irradiance distribution indicates a high degree of uniformity of the irradiance distribution in the fiber core 350 (e.g. optimal core irradiance distribution).

FIG. 28 shows the out-coupled longitudinally radially-symmetric irradiance distribution along the outer surface of the light diffusing section 308 (e.g., the diffusing irradiance distribution) of this exemplary embodiment of the device 300. The diffusing irradiance distribution shows the optimal "top hat" irradiance distribution indicating spatial uniformity of the out-coupled longitudinally radially-symmetric irradiance along the outer surface of the light diffusing section 308. The horizontal axis of FIG. 28 shows longitudinal length in mm and the horizontal arrow indicates the longitudinal length of the light diffusing section 308. The vertical axis of FIG. 28 shows the out-coupled irradiance at the surface of the light diffusing section 308 measured in Watts/cm$^2$ at a distance 0.75 mm from the central axis.

Example IV

In an exemplary embodiment and referring to FIGS. 11 and 12, the device 300 includes the non-circular core fiber 302, the lead-in optical fiber 304, the at least one optical connector 306. During operation, the lead-in optical fiber 304 is in light communication to (i) a light source (not shown) and (ii) the non-circular core fiber 302 via the at least one optical connector 306. The lead-in fiber 304 has a 200 µm OD glass core and a 230 µm OD cladding. The length of the non-circular core fiber 302 is 30 cm, which distally terminates into the light blocking means 314 made out of a reflecting coating of aluminum deposition.

Referring to FIG. 12, the non-circular core fiber 302 includes the fiber core 350 constructed out of PMMA with a hexagonal geometry in a circumscribed ø660 µm diameter circle. The fiber core 350 is cladded by the cladding 352 with an interior surface geometry 356 that is same hexagonal geometry as the fiber core 350. However, the exterior surface geometry 354 of the cladding 352 is circular. The cladding 352 is constructed of a polymer with a ø740 µm OD. The non-circular core fiber 302 further includes the enclosed open cavity 358 and the covering 360. The covering 360 is constructed of a translucent Pebax® resin with a ø1000 µm OD and a ø900 µm ID. The covering is heat sealed at one or both of its ends.

The non-circular core fiber 302 further includes the light diffusing section 308 having the diffusing proximal end 310 and the diffusing distal end 312. The light diffusing section 308 is exactly the same as the light diffusing section 308 of the embodiment described above in Example III including its internal scattering features 362.

FIG. 35 shows a map of the irradiance at the vertical cross-section (shown as "316" in FIG. 11) through the fiber core 350 taken just before the diffusing proximal end 310 for this exemplary embodiment of the device 300. The light source used is a 690 nm laser with 0.125 Watt launch power and this power was adjusted until the irradiance measured until the irradiance measured at the center 307 of the longitudinal length of the light diffusing section 308 was 150 mW/cm$^2$. This measurement is taken 0.75 mm from the central axis of the stated location of the light diffusion section 308. The total length of optical fiber (combination of the lead-in fiber 304 and the non-circular core fiber 302) from the light source leading up to this location 316 is 2 meters long. During operation, the non-circular core fiber 302 is filled with laser light having an angular distribution of a NA of 0.22.

The associated irradiance distribution graphs shown in FIG. 35 taken from vertical and horizontal cross sections through the center of the map of the irradiance show the same "top hat" core irradiance distribution as the above-discussed conventional cylindrical light diffusing device 200 with a mode mixer (24). This "top hat" core irradiance distribution indicates a high degree of uniformity of the irradiance distribution in the fiber core 350.

FIG. 36 shows the out-coupled longitudinally radially-symmetric irradiance distribution along the outer surface of the light diffusing section 308 (e.g., the diffusing irradiance distribution) of this exemplary embodiment of the device 300. The diffusing irradiance distribution shows the optimal "top hat" irradiance distribution indicating spatial uniformity of the out-coupled longitudinally radially-symmetric irradiance along the outer surface of the light diffusing section 308. The horizontal axis of FIG. 36 shows longitudinal length in mm and the horizontal arrow indicates the longitudinal length of the light diffusing section 308. The vertical axis of FIG. 36 shows the out-coupled irradiance at the surface of the light diffusing section 308 measured in Watts/cm$^2$ at a distance 0.75 mm from the central axis.

Example V

Figure 43:
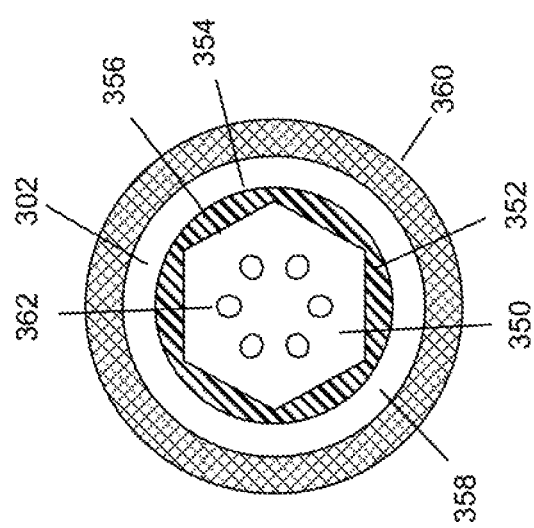
FIG. 43 is a vertical cross-sectional view of a non-circular core fiber exemplary embodiment accordingly to the present invention at a location right before the diffusing proximate end of the light diffusing section.

In an exemplary embodiment and referring to FIGS. 11 and 43, the device 300 includes the non-circular core fiber 302, the lead-in optical fiber 304, the at least one optical connector 306. During operation, the lead-in optical fiber 304 is in light communication to (i) a light source (not shown) and (ii) the non-circular core fiber 302 via the at least one optical connector 306. The lead-in fiber 304 has a 200 µm OD glass core and a 230 µm OD cladding. The length of the non-circular core fiber 302 is 30 cm, which distally terminates into the light blocking means 314 made out of a reflecting coating of aluminum deposition.

Referring to FIG. 43, the non-circular core fiber 302 includes the fiber core 350 constructed out of glass with a hexagonal geometry in a circumscribed ø460 µm diameter circle. The fiber core 350 is cladded by the cladding 352 with an interior surface geometry 356 that is same hexagonal geometry as the fiber core 350. However, the exterior surface geometry 354 of the cladding 352 is circular. The cladding 352 is constructed of a glass with a ø480 µm OD. The non-circular core fiber 302 further includes the enclosed open cavity 358 and the covering 360. The covering 360 is constructed of a translucent Pebax® resin with a ø1000 µm OD and a ø800 µm ID. The covering is heat sealed at one or both of its ends.

The non-circular core fiber 302 further includes the light diffusing section 308 having the diffusing proximal end 310 and the diffusing distal end 312. The light diffusing section 308 is 11.3 mm in longitudinal length and the internal scattering features 362 begin at the diffusing proximal end 310 and ends at the diffusing distal end 312. The features 362 are comprised of 37 sets of 6 ellipses. Each ellipse is approximately spherical with a 40 µm diameter and is located 100 um from the central axis of the fiber core 350 and distributed at 60° increments as shown in FIG. 43. The 37 sets of the features 362 are arranged based upon the following formula in a non-linear fashion: $z_i=0.35i+0.00015i^2-0.000032i^3$ where the index i is an integer with values from 0 to 36 and $z_i$ is the relative z location of the $i^{th}$ feature 362 along the axis 364. Please note that the present invention is not limited to this formula, the size of the features 362, the number of features 362 per unit length of the diffusing section 308, or the amount of scattering per feature 362. Instead, the present invention includes other suitable spacing's, sizes, numbers of features 362 per unit length, and amounts of scattering per feature 362.

The light source and the total length are exactly the same as the embodiment described above in Example IV and the map of the irradiance at the vertical cross-section 316 is substantially identical to that shown in FIG. 35. When the source is adjusted in the same fashion as in Example IV, the diffusing irradiance distribution shows an optimal "top hat" irradiance distribution that is substantially similar as shown in FIG. 36.

Please note that unless otherwise expressly stated, all diffusing irradiance distribution data presented in this specification and drawings (e.g., FIGS. 2-3, 5-6, 27-28, 34-36) are taken 0.75 mm from the central axis of the applicable location of either the fiber core or the diffuser.

The method of the present invention further includes applying a photosensitive drug composition to desired treatment site; placing the device (300, 400) described interstitially inside the desired treatment site and applying light delivered by the device 300 to the treatment site at a wavelength absorbed by the photosensitive drug composition so as to inhibit targeted cells located within the treatment site.

Although there has been hereinabove described a fiber optic light diffusing device and method for PIT, PDT and other light activated therapies in accordance with the present invention, for purposes of illustrating the manner in which the invention may be used to advantage, it will be appreciated that the invention is not limited thereto. Accordingly, any and all modifications, variations, or equivalent arrangements which may occur to those skilled in the art should be considered to be within the scope of the present invention as defined in the appended claims.

What is claimed:

1. A frontal light diffusing device for delivering a predetermined optical irradiance value to a targeted area comprising:
   i) an optical fiber having a proximal end and a distal termination having a light output face;
   ii) a collimation lens assembly having a collimation lens and a variable aperture that blocks non-central portions of light outcoupled from the light output face, thereby allowing only a central portion of the light to exit through the variable aperture resulting in a flat irradiance distribution which means that the central portion of the light exiting through the variable aperture is a collimated light output having a "top hat" spatial irradiance distribution with less than +/−20% difference in irradiance between near field, far field, and distance between the near field and the far field.

2. The frontal light diffusing device of claim 1 wherein the collimated light output has a "top hat" spatial irradiance distribution with less than +/−15% difference in irradiance between near field, far field, and distance between the near field and the far field.

3. The frontal light diffusing device of claim 1 wherein the collimated high output has a "top hat" spatial irradiance distribution with less than +/−10% difference in irradiance between near field, far field, and distance between the near field and the far field.

4. The frontal light diffusing device of claim 1 wherein the light outcoupled from the light output face overfills the collimating lens and the non-central portions of light are blocked, reflected or absorbed.

5. The frontal light diffusing device of claim 1 wherein the collimation lens constructed out of a transparent optical material.

6. The frontal light diffusing device of claim 5 wherein the optical material has a graded index profile.

7. The frontal light diffusing device of claim 1 wherein the collimation lens constructed out of one or more materials selected from the group consisting of glass, crystal, transparent polymer, and reflective material.

8. The frontal light diffusing device of claim 1 wherein the collimation lens constructed out of a transparent polymer.

9. The frontal light diffusing device of claim 1 wherein the collimation lens constructed out of glass.

10. The frontal light diffusing device of claim 1 wherein at least one surface of the collimation lens is selected from the group consisting of spherical surface, aspherical surface, refractive surface, diffractive surface, reflective surface, and a combination thereof.

11. The frontal light diffusing device of claim 1 wherein at least one surface of the collimation lens is a spherical surface.

12. The frontal light diffusing device of claim 1 wherein at least one surface of the collimation lens is an aspherical surface.

13. The frontal light diffusing device of claim 1 wherein at least one surface of the collimation lens is a combination of optical elements providing a refractive aspherical surface.

14. The frontal light diffusing device of claim 1 wherein at least one surface of the collimation lens is a combination of optical elements providing a refractive spherical surface.

15. The frontal light diffusing device of claim 1 wherein the collimation lens includes multiple optical elements.

16. The front light diffusing device of claim 1 wherein the optical fiber is a cylindrical fiber.

17. The front light diffusing device of claim 1 wherein the optical fiber includes a non-circular fiber core.

18. The frontal light diffusing device of claim 1 wherein the variable aperture is an iris that allows the central portion of light that exits through the variable aperture to have a beam size from 1 mm to 12 mm in diameter.

19. The frontal light diffusing device of claim 1 wherein the variable aperture is configured so that the central portion of the light that exits through the variable aperture to be in a square or rectangular shape.

20. The frontal light diffusing device of claim 1 wherein the variable aperture is configured so that the central portion of the light that exits through the variable aperture to be in a non-symmetric shape.

21. A frontal light diffusing device for delivering a predetermined optical irradiance value to a targeted area comprising:
   i) an optical fiber having a proximal end, a distal end having a light output face, an optical axis, a fiber core with a core diameter of 400 um, and a cladding with a diameter of 430 um;
   ii) a collimation lens assembly having a collimation lens that is a plano-convex lens with a 25 mm diameter and a focal length of 75 mm; and
   iii) the collimation lens assembly further includes a variable aperture that blocks non-central portions of light outcoupled from the light output face of the distal end of the optical fiber, thereby allowing only a central portion of the light to exit through the variable aperture is a collimated light output having a flat irradiance distribution.

22. The frontal light diffusing device of claim 21 where the flat irradiance distribution is a "top hat" spatial irradiance distribution with less than +/−20% difference in irradiance between in near field, far field, and distance between the near field and the far field.

23. The front light diffusing device of claim 21 wherein the optical fiber is a cylindrical fiber.

24. The front light diffusing device of claim 21 wherein the optical fiber includes a non-circular fiber core.

25. The frontal light diffusing device of claim 21 wherein the collimation lens includes a back focal length and the light output face of the distal end of the optical fiber is located at the back focal length of the collimation lens.

26. The frontal light diffusing device of claim 21 wherein the collimation lens assembly includes a collimation lens constructed out of one or more materials selected from the group consisting of glass, crystal, transparent polymer, and reflective material.

27. The frontal light diffusing device of claim 21 wherein at least one surface of the collimation lens is selected from the group consisting of spherical surface, aspherical surface, refractive surface, diffractive surface, reflective surface, and a combination thereof.

* * * * *